(12) United States Patent
Zocca et al.

(10) Patent No.: US 7,273,053 B2
(45) Date of Patent: *Sep. 25, 2007

(54) MONITORING AND CONTROL FOR A LARYNGEAL MASK AIRWAY DEVICE

(76) Inventors: Mario Zocca, Via Lanificio 24, 37033 Montorio Veronese (Verona) (IT); Archibald I. J. Brain, Osprey House, 5 Old Street, St. Helier (BE); Paolo Mozzo, Via Lazzaretto 59B, 37133 Verona (IT)

( * ) Notice: Subject to any disclaimer, the term of this patent is extended or adjusted under 35 U.S.C. 154(b) by 364 days.

This patent is subject to a terminal disclaimer.

(21) Appl. No.: 10/335,627

(22) Filed: Jan. 2, 2003

(65) Prior Publication Data

US 2003/0101998 A1    Jun. 5, 2003

Related U.S. Application Data

(63) Continuation of application No. 09/382,030, filed as application No. PCT/GB98/03849 on Dec. 21, 1998, now abandoned.

(30) Foreign Application Priority Data

Dec. 24, 1997   (GB) ................................ 9727367.6

(51) Int. Cl.
*A61M 16/00* (2006.01)
(52) U.S. Cl. ............................. 128/207.14; 128/207.15
(58) Field of Classification Search .......... 128/207.15, 128/207.14, 200.26, 203.12, 204.23, 204.21, 128/205.23, 203.13, 204.18, 200.24, 207.16; 604/100.01, 100.02, 100.03
See application file for complete search history.

(56) References Cited

U.S. PATENT DOCUMENTS 2,862,498 A     12/1958   Weekes ...................... 128/351

(Continued)

FOREIGN PATENT DOCUMENTS

CA           2067782           6/1999

(Continued)

OTHER PUBLICATIONS

Brain, "The laryngeal mask airway—a possible new solution to airway problems in the emergency situation," *Archives of Emergency Medicine*, 1984, 1, 229-232.

(Continued)

*Primary Examiner*—Teena Mitchell
(74) *Attorney, Agent, or Firm*—Wilmer, Cutler, Pickering Hale and Dorr LLP

(57) ABSTRACT

A reversibly operable motor is mechanically connected to automatically position the piston of an air syringe that is pneumatically connected to the inflatable/deflatable seal ring or cuff of a laryngeal mask airway device (LMA) that is installed in a patient, who is being ventilated and/or anaesthetized via the airway of the LMA device. Air pressure in the cuff corrected as necessary to conform to a predetermined pressure level. The system continuously monitors for abnormal patterns of response, with audibly and visually reported warnings to the anaesthetist; these warnings include system detection of a patient's incipient sign of premature awareness while still under surgery, system detection and warning of a system or LMA malfunction, and continual microprocessor survey and integration of historical data to determine decremental recovery from administered anaesthesia.

8 Claims, 12 Drawing Sheets

U.S. PATENT DOCUMENTS

| | | | |
|---|---|---|---|
| 3,529,596 A | 9/1970 | Garner | 128/207.15 |
| 3,554,673 A | 1/1971 | Schwartz et al. | 417/412 |
| 3,683,908 A | 8/1972 | Michael et al. | |
| 3,794,036 A | 2/1974 | Carroll | 128/207.15 |
| 3,931,822 A | 1/1976 | Marici | |
| 4,067,329 A | 1/1978 | Winicki et al. | |
| 4,104,357 A | 8/1978 | Blair | |
| 4,116,201 A | 9/1978 | Shah | 128/207.15 |
| 4,134,407 A | 1/1979 | Elam | 128/202.22 |
| 4,159,722 A | 7/1979 | Walker | 137/496 |
| 4,178,938 A | 12/1979 | Au | 128/207.15 |
| 4,178,940 A | 12/1979 | Au | 128/207.15 |
| 4,231,365 A | 11/1980 | Scarberry | 128/207.15 |
| 4,256,099 A | 3/1981 | Dryden | |
| 4,285,340 A | 8/1981 | Gesari et al. | 128/205.24 |
| 4,351,330 A | 9/1982 | Scarberry | |
| 4,471,775 A | 9/1984 | Clair et al. | 128/205.24 |
| 4,501,273 A | 2/1985 | McGinnis | 128/207.15 |
| 4,509,514 A | 4/1985 | Brain | 128/207.15 |
| 4,526,196 A | 7/1985 | Pistillo | 137/557 |
| 4,553,540 A | 11/1985 | Straith | |
| 4,583,917 A | 4/1986 | Shah | 417/63 |
| 4,630,606 A | 12/1986 | Weerda et al. | 128/207.14 |
| 4,689,041 A | 8/1987 | Corday et al. | 604/509 |
| 4,770,170 A | 9/1988 | Sato et al. | 128/207.15 |
| 4,793,327 A | 12/1988 | Frankel | |
| 4,825,862 A | 5/1989 | Sato et al. | 128/207.15 |
| 4,832,020 A | 5/1989 | Augustine | |
| 4,850,349 A | 7/1989 | Farahany | 128/207.15 |
| 4,856,510 A | 8/1989 | Kowalewski | 128/207.15 |
| 4,872,483 A | 10/1989 | Shah | 137/557 |
| 4,924,862 A | 5/1990 | Levinson | 128/207.16 |
| 4,953,547 A | 9/1990 | Poole, Jr. | 128/203.12 |
| 4,981,470 A | 1/1991 | Bombek, IV | 600/350 |
| 4,995,388 A | 2/1991 | Brain | 128/207.15 |
| 5,038,766 A | 8/1991 | Parker | 128/200.26 |
| 5,042,469 A | 8/1991 | Augustine | |
| 5,042,476 A | 8/1991 | Smith | 128/207.14 |
| 5,203,320 A | 4/1993 | Augustine | |
| 5,218,970 A | 6/1993 | Turnbull et al. | 128/207.15 |
| 5,235,973 A * | 8/1993 | Levinson | 128/207.15 |
| 5,241,956 A | 9/1993 | Brain | 128/207.15 |
| 5,249,571 A | 10/1993 | Brain | 128/207.14 |
| 5,273,537 A | 12/1993 | Haskvitz | 604/99.01 |
| 5,277,178 A | 1/1994 | Dingley et al. | |
| 5,282,464 A | 2/1994 | Brain | 128/207.15 |
| 5,297,547 A | 3/1994 | Brain | 128/207.15 |
| 5,303,697 A | 4/1994 | Brain | 128/200.26 |
| 5,305,743 A | 4/1994 | Brain | 128/207.15 |
| 5,311,861 A | 5/1994 | Miller | 128/201.13 |
| 5,331,967 A | 7/1994 | Akerson | 128/207.15 |
| 5,339,805 A | 8/1994 | Parker | 128/200.26 |
| 5,339,808 A | 8/1994 | Don Michael | 128/207.15 |
| 5,355,879 A | 10/1994 | Brain | 128/207.15 |
| 5,361,753 A | 11/1994 | Pothman et al. | 128/207.15 |
| 5,391,248 A | 2/1995 | Brain | 156/242 |
| 5,452,715 A | 9/1995 | Boussignac | 128/207.15 |
| 5,459,700 A | 10/1995 | Jacobs | 368/10 |
| 5,487,383 A | 1/1996 | Levinson | |
| 5,529,582 A | 6/1996 | Fukuhara | 606/205 |
| 5,546,935 A * | 8/1996 | Champeau | 128/205.23 |
| 5,551,420 A | 9/1996 | Lurie et al. | 128/205.13 |
| 5,569,219 A | 10/1996 | Hakki et al. | 604/282 |
| 5,577,693 A * | 11/1996 | Corn | 248/176.1 |
| 5,582,167 A | 12/1996 | Joseph | |
| 5,584,290 A * | 12/1996 | Brain | 128/207.15 |
| 5,599,301 A | 2/1997 | Jacobs et al. | 604/65 |
| 5,623,921 A | 4/1997 | Kinsinger et al. | 128/200.26 |
| 5,626,151 A | 5/1997 | Linden | 128/897 |
| 5,632,271 A | 5/1997 | Brain | 128/207.15 |
| RE35,531 E | 6/1997 | Callaghan et al. | 128/207.15 |
| 5,653,229 A | 8/1997 | Greenberg | 128/207.15 |
| 5,655,528 A | 8/1997 | Pagan | 128/207.14 |
| 5,682,880 A | 11/1997 | Brain | 128/207.15 |
| 5,692,498 A | 12/1997 | Lurie et al. | 128/205.24 |
| 5,694,929 A | 12/1997 | Christopher | |
| 5,711,293 A | 1/1998 | Brain | 128/200.24 |
| 5,738,094 A | 4/1998 | Hoftman | |
| 5,743,254 A | 4/1998 | Parker | 128/200.26 |
| 5,743,258 A * | 4/1998 | Sato et al. | 128/207.15 |
| 5,746,202 A | 5/1998 | Pagan | 128/207.14 |
| 5,771,889 A | 6/1998 | Pagan | 128/207.15 |
| 5,778,872 A | 7/1998 | Fukunaga et al. | 128/202.27 |
| 5,791,341 A | 8/1998 | Bullard | 128/207.15 |
| 5,816,240 A * | 10/1998 | Komesaroff | 128/200.23 |
| 5,819,723 A | 10/1998 | Joseph | 128/207.14 |
| 5,832,916 A | 11/1998 | Lundberg et al. | |
| 5,850,832 A | 12/1998 | Chu | 128/200.26 |
| 5,855,203 A * | 1/1999 | Matter | 128/207.14 |
| 5,860,418 A | 1/1999 | Lundberg | 128/202.22 |
| 5,865,176 A | 2/1999 | O'Neil | 128/207.15 |
| 5,878,745 A | 3/1999 | Brain | 128/207.15 |
| 5,881,726 A | 3/1999 | Neame | 128/207.15 |
| 5,893,891 A | 4/1999 | Zahedi | 128/200.24 |
| 5,896,858 A | 4/1999 | Brain | 128/207.15 |
| 5,915,383 A | 6/1999 | Pagan | 128/207.15 |
| 5,937,860 A * | 8/1999 | Cook | 128/207.15 |
| 5,957,133 A | 9/1999 | Hart | |
| 5,979,445 A | 11/1999 | Neame et al. | 128/207.15 |
| 5,983,891 A | 11/1999 | Fukunaga | |
| 5,983,894 A | 11/1999 | Fukunaga et al. | 128/205.29 |
| 5,983,896 A * | 11/1999 | Fukunaga et al. | 128/207.14 |
| 5,983,897 A | 11/1999 | Pagan | 128/207.15 |
| 5,988,167 A | 11/1999 | Kamen | 128/207.15 |
| 5,996,582 A * | 12/1999 | Turnbull | 128/207.29 |
| 6,003,510 A | 12/1999 | Anunta | 128/200.26 |
| 6,003,511 A * | 12/1999 | Fukunaga et al. | 128/202.27 |
| 6,003,514 A | 12/1999 | Pagan | 128/207.15 |
| 6,012,452 A | 1/2000 | Pagan | 128/200.26 |
| 6,021,779 A | 2/2000 | Pagan | 128/207.15 |
| 6,050,264 A | 4/2000 | Greenfield | 128/207.15 |
| 6,062,219 A | 5/2000 | Lurie et al. | 128/205.24 |
| 6,070,581 A | 6/2000 | Augustine et al. | 128/207.15 |
| 6,079,409 A | 6/2000 | Brain | 128/200.26 |
| D429,811 S | 8/2000 | Bermudez | D24/110.5 |
| 6,095,144 A | 8/2000 | Pagan | 128/207.15 |
| 6,098,621 A | 8/2000 | Esnouf | 128/204.23 |
| 6,110,143 A * | 8/2000 | Kamen | 604/97.02 |
| 6,116,243 A | 9/2000 | Pagan | 128/207.15 |
| 6,119,695 A | 9/2000 | Augustine et al. | 128/207.15 |
| 6,131,571 A * | 10/2000 | Lampotang et al. | 128/204.21 |
| 6,149,603 A | 11/2000 | Parker | |
| 6,155,257 A * | 12/2000 | Lurie et al. | 128/204.23 |
| 6,213,120 B1 * | 4/2001 | Block et al. | 128/204.23 |
| 6,224,562 B1 | 5/2001 | Lurie et al. | 601/41 |
| 6,234,985 B1 | 5/2001 | Lurie et al. | 601/41 |
| 6,240,922 B1 | 6/2001 | Pagan | |
| 6,251,093 B1 | 6/2001 | Valley et al. | 604/97.03 |
| 6,269,813 B1 | 8/2001 | Fitzgerald | 128/207.16 |
| 6,315,739 B1 * | 11/2001 | Merilainen et al. | 600/587 |
| 6,390,093 B1 | 5/2002 | Mongeon | |
| 6,427,686 B2 | 8/2002 | Augustine et al. | |
| 6,439,232 B1 | 8/2002 | Brain | |
| 6,450,164 B1 * | 9/2002 | Banner et al. | 128/204.21 |
| 6,631,720 B1 | 10/2003 | Brain et al. | |
| 6,647,984 B1 * | 11/2003 | O'Dea | 128/207.16 |
| 6,651,666 B1 * | 11/2003 | Owens | 128/207.16 |
| 6,705,318 B1 | 3/2004 | Brain | |
| 7,004,169 B2 | 2/2006 | Brain et al. | |
| 7,040,322 B2 * | 5/2006 | Fortuna | 128/207.15 |
| 7,051,736 B2 * | 5/2006 | Banner et al. | 128/204.21 |
| 7,096,868 B2 * | 8/2006 | Tateo et al. | 128/207.15 |
| 7,156,100 B1 | 1/2007 | Brain et al. | |
| 2003/0051734 A1 | 3/2003 | Brain | |

| | | |
|---|---|---|
| 2003/0131845 A1 | 7/2003 | Lin |

FOREIGN PATENT DOCUMENTS

| | | |
|---|---|---|
| CA | 2012750 | 8/1999 |
| EP | 0 389 272 | 9/1990 |
| EP | 0 402 872 | 12/1990 |
| EP | 0 294 200 | 4/1992 |
| EP | 0 580 385 | 5/1996 |
| EP | 0 712 638 | 5/1996 |
| EP | 0 732 116 | 9/1996 |
| EP | 0 796 631 | 9/1997 |
| EP | 0 845 276 | 6/1998 |
| EP | 0 865 798 | 9/1998 |
| EP | 0 922 465 | 6/1999 |
| EP | 1125595 | 8/2001 |
| EP | 1 119 386 B1 | 9/2005 |
| GB | 2111394 | 12/1982 |
| GB | 2205499 | 6/1987 |
| GB | 2298797 A | 9/1996 |
| GB | 2317342 | 8/1997 |
| GB | 2317830 | 9/1997 |
| GB | 2318735 | 10/1997 |
| GB | 2319478 | 10/1997 |
| GB | 2321854 | 1/1998 |
| GB | 2323289 | 2/1998 |
| GB | 2323290 | 3/1998 |
| GB | 2323291 | 3/1998 |
| GB | 2323292 | 3/1998 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO91/03207 | 3/1991 |
| WO | WO 91/03207 | 3/1991 |
| WO | WO 91/07201 | 5/1991 |
| WO | WO91/07201 | 5/1991 |
| WO | WO91/12845 | 9/1991 |
| WO | WO-91/12845 | 9/1991 |
| WO | WO-92/13587 | 8/1992 |
| WO | WO92/13587 | 8/1992 |
| WO | WO 92/13587 | 8/1992 |
| WO | WO 95/33506 | 12/1995 |
| WO | WO95/33506 | 12/1995 |
| WO | WO 97/12640 | 4/1997 |
| WO | WO97/12640 | 4/1997 |
| WO | WO 97/12641 | 4/1997 |
| WO | WO97/12641 | 4/1997 |
| WO | WO98/16273 | 4/1998 |
| WO | WO 98/16273 | 4/1998 |
| WO | WO99/06093 | 2/1999 |
| WO | WO 99/06093 | 2/1999 |
| WO | WO-00/09189 | 2/2000 |
| WO | WO 00/22985 | 4/2000 |
| WO | WO 00/23135 | 4/2000 |
| WO | WO 00/61212 | 10/2000 |

OTHER PUBLICATIONS

Brain, "The laryngeal mask airway," *Anaesthesia*, 1985, vol. 40, pp. 356-361.
Brain, "Three cases of difficult intubation overcome by the laryngeal mask airway," *Anaesthesia*, 1985, vol. 40, pp. 353-355.
DeMello, et al., "The use of the laryngeal mask airway in primary anaesthesia," *Anaesth. Corresp.* (1990) 45,9:793.
Hickey, et al., "Cardiovascular response to insertion to Brain's laryngeal mask," *Anaesthesia* 1990, vol. 45, pp. 629-633.
Davies, et al., "Laryngeal mask airway and tracheal tube insertion by unskilled personnel," *The Lancet*, vol. 336, pp. 977-979.
Brain, "The Laryngeal Mask-A New Concept in Airway Management," *Br. J.Anaesth*, (1983), 55, 801-805.
Brodrick et al., "The laryngeal mask airway," *Anaesthesia*, 1989, vol. 44, pp. 238-241.
Inomata, et al., "Transient Bilateral Vocal Cord Paralysis after Insertion of a Laryngeal Mask Airway," *Anesthesiology*, 82:787-788, 1995.
Majumder, et al., "Bilateral Lingual nerve Injury following the use of the laryngeal mask airway," *Anaesthesia*, 1998, 53, pp. 184-186.
Wynn, et al., "Tongue Cyanosis after Laryngeal Mask Airway Insertion," *Anesthesiology*, V. 80, No. 6, Jun. 1994, p. 1403.
Nagai, "Unilateral hypoglossal nerve paralysis following the use of the laryngeal mask airway," *Anaesthesia*, 1994, vol. 49, pp. 603-604.
Brain, et al., "A new laryngeal mask prototype," *Anasethesia*, 1995, vol. 50, pp. 42-48.
Burgard, et al., The Effect of Laryngeal Mask Cuff Pressure on Postoperative Sore Throat Incidence, *J. of Clinical Anesthesia* 8:198-201, 1996.
Benumof, "Laryngeal Mask Airway and the ASA Difficult Airway Algorithm," *Anesthesiology* 1996:v84 No. 3:686-99.
Pennant, "Comparison of the Endotracheal Tube and Laryngeal Mask in Airway Management by Paramedical Personnel," *Anesth Analg* 1992:74:531-4.
Brimacombe, "The split laryngeal mask airway," p. 639.
Worthington, et al., "Proceedings of the Anaesthetic Research Society," *Br. J. of Anaesthesia* 1995 75:228P-229P.
Heath, "Endotracheal intubation through the Laryngeal Mask—helpful when laryngoscopy is difficult or dangerous," *European Journal of Anaesthesiology* 1991, Suppl. 4, 41-45.
Kambic, et al., "Intubation Lesions of the Larynx," *Br. J. Anasth.* 1978, 50, 587-590.
Abdelatti, "A cuff pressure controller for tracheal tubes and laryngeal mask airway," *Anaesthesia*, 1999, 54 pp. 981-986.
Muthuswamy, et al., "The Use of Fuzzy Integrals and Bispectral Analysis of the Electroencephalogram to Predict Movement Under Anesthesia," *IEEE Transactions on Biomedical Engineering*, vol. 46, No. 3, Mar. 1999, pp. 290-299.
Glen, "The development of 'Diprifusor': a TCI system for propofol," *Anaesthesia* 1998, 53, Suppl. 1, pp. 13-21.
Gray et al., "Development of the technology for 'Diprifusor' TCI systems," *Anaesthesia* 1998, 53, Suppl. 1, pp. 22-27.
Engbers, "Practical use of 'Diprifusor' systems", *Anaesthesia* 1998, 53, Suppl. 1, pp. 28-34.
Doyle et al., "Intraoperative Awareness: A Continuing Clinical Problem," http://doyle.ibme.utoronto.ca/anesthesia/aware.htm.
Eriksson, et al., "Functional Assessment of the Pharynx at Rest and during Swallowing in Partially Paralyzed Humans," *Anesthesiology* vol. 87, No. 5, Nov. 1987, pp. 1035-1042.
Cuff-Pressure-Control CDR 2000, LogoMed.
Seegobin, et al., "Endotracheal cuff pressure and tracheal mucosal blood flow: endoscopic study of effects of four large volume cuffs," *British Medical Journal*, vol. 288, Mar. 31, 1984.
Raeder, et al., "Tracheal tube cuffs pressures," *Anaesthesia*, 1985, vol. 40, pp. 444-447.
Jacobson et al., A Study of Intracuff Pressure Measurements, Trends and Behaviours in Patients During Prolonged Periods of Tracheal Intubation, *Br. J. Anaesth.* 1981, 53, 97.
Willis, et al., "Tracheal tube cuff pressure," *Anaesthesia*, 1988, vol. 43, pp. 312-314.
Miller, "A pressure regulator for the cuff of a tracheal tube," *Anaesthesia*, 1992, vol. 47, pp. 594-596.
Patel, et al, "Tracheal tube cuff pressure," *Anaesthesia*, 1984, vol. 39, pp. 862-864.
Pippin, et al., "Long-term tracheal intubation practice in the United Kingdom", *Anaesthesia*, 1983, vol. 38, pp. 791-795.
Bernhard, et al., "Adjustment of Intracuff Pressure to Prevent Aspiration," *Anesthesiology* v. 50 No. 4:363-366, 1979.

Bernhard, et al., "Physical Characteristics of and Rates of Nitrous Oxide Diffusion into Tracheal Tube Cuffs," *Anesthesiology* 48:413-417 1978.

Craven, "Prevention of Hospital-Acquired Pneumonia: Measuring Effect in Ounces, Pounds, and Tons," *Annals of Internal Medicine*, vol. 122, No. 3, pp. 229-231 Feb. 1, 1995.

Lindholm, "Prolonged Endotracheal Intubation," *ACTA Anaesthesiologica Scandinavica* 1969 vol. 33 32-46.

Martin, Todd, "Patentability of Methods of Medical Treatment: A Comparative Study," Jun. 200, pp. 381-423.

"Improving Anaesthesia"; Med Pro Monthly; Nov.-Dec. 1998; pp. 311-312.

Rieger, et al.; Anesthesiology, vol. 87, No. 1; Jul. 1997.

Index; Laryngeal Mask Publications; 74 Pages; Dec. 1998; www.saga.nl/lma/lmapubl.htm.

"Neurometric Assessment of Adequacy of Intraoperative Anesthetic"; Mar. 1999; 3 pages; www/pnl.gov/medical/info/neuro.htm.

Caplan et al., "Adverse Respiratory Events in Anesthesia: A Closed Claims Analysis"; Anesthesiology, vol. 72, pp. 828-833, 1990.

Communication of a notice of opposition, European Patent Office, Feb. 15, 2006 (cover page and pp. 1-4).

European Patent Office, International Search Report for PCT/GB98/03849 (WO 99/33508) mailed Mar. 31, 1999, 4 pages.

Observations by Third Party Concerning European Patent Application No. 99 947 765.6-2318, European Patent Office, Munich, Germany, Jan. 18, 2005, (3 pages).

Response to Complaint Matter No. 4b 0 440-05, In the Matter of: LMA Deutschland GmbH versus Ambu (Deutschland) GmbH, Feb. 10, 2006, pp. 1-47.

Rieger et al., Anesthesiology, vol. 87, No. 1, Jul. 1997.

* cited by examiner

SAMPLE DISPLAY OF THE PERCENT AWAKENING FEATURE

RELATIVELY LOW MUSCLE ACTIVITY

SAMPLE DISPLAY OF THE PERCENT AWAKENING FEATURE

RELATIVELY HIGH MUSCLE ACTIVITY

AUDIBLE AND VISUAL ALARMS WILL ISSUE WHEN THE PERCENTAGE REACHES 100%

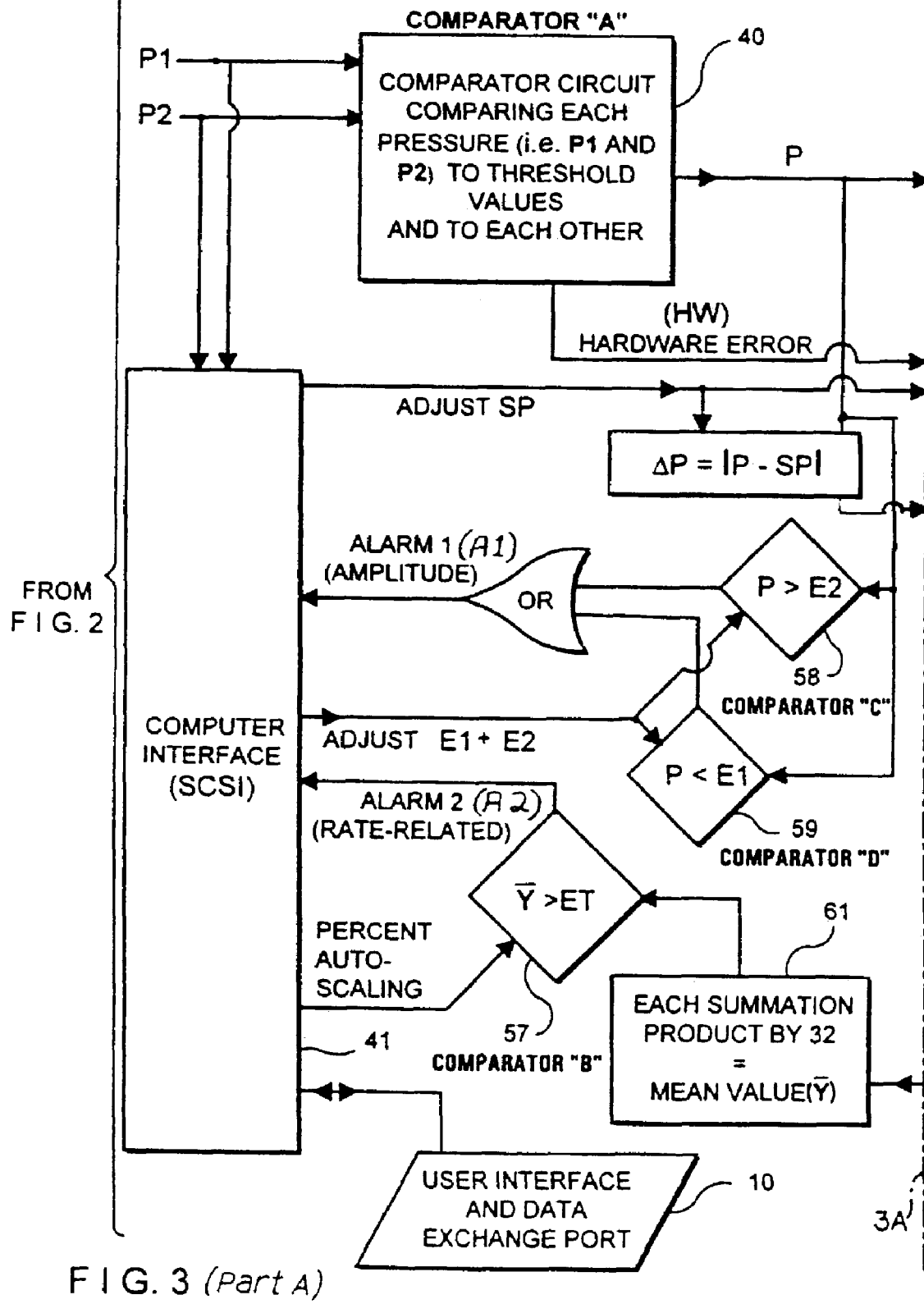
FIG. 3 (Part A)

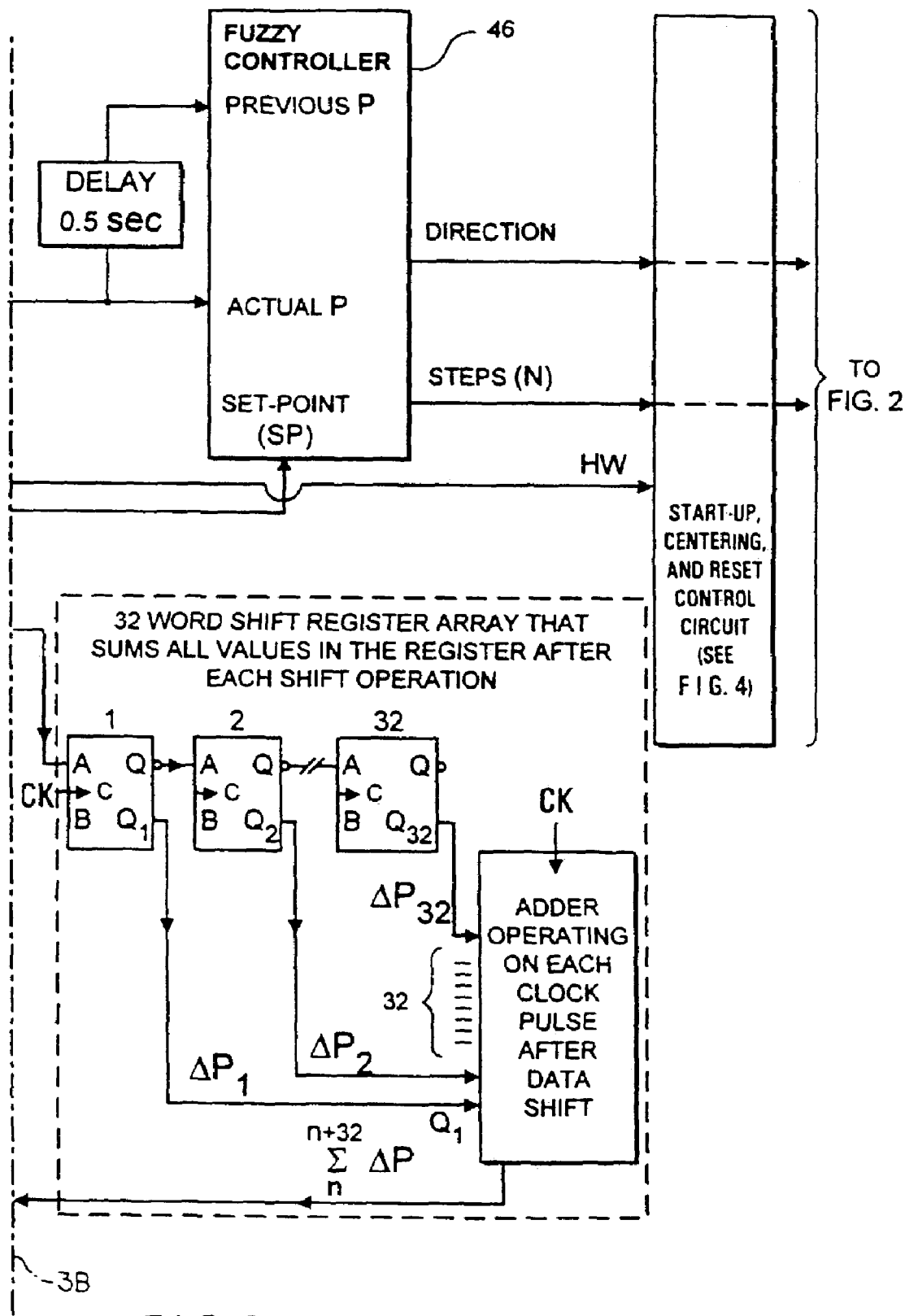
FIG. 3 (Part B)

Set Points at E1 = -3 and E2 = 3 (and symmetrical around SP)

| Amplitude Alarm Settings | | Derived Rate-Related Alarm Value: | |
|---|---|---|---|
| E1 | -3 | ET | 1.5 |
| E2 | 3 | | |

| | Empirical Values: | | | Calculated Values: | | |
|---|---|---|---|---|---|---|
| Time | Actual P | Set Point (SP) | Deviation from SP | Absolute Value of deviation | 32-Bit Summation | Alarm 2 (1=Yes) |
| 0 | 51 | 50 | 1 | 1 | n.a. | n.a. |
| 1 | 52 | 50 | 2 | 2 | n.a. | n.a. |
| 2 | 54 | 50 | 4 | 4 | n.a. | n.a. |
| 3 | 55 | 50 | 5 | 5 | n.a. | n.a. |
| 4 | 49 | 50 | -1 | 1 | n.a. | n.a. |
| 5 | 45 | 50 | -5 | 5 | n.a. | n.a. |
| 6 | 47 | 50 | -3 | 3 | n.a. | n.a. |
| 7 | 49 | 50 | -1 | 1 | n.a. | n.a. |
| 8 | 51 | 50 | 1 | 1 | n.a. | n.a. |
| 9 | 53 | 50 | 3 | 3 | n.a. | n.a. |
| 10 | 50 | 50 | 0 | 0 | n.a. | n.a. |
| 11 | 45 | 50 | -5 | 5 | n.a. | n.a. |
| 12 | 43 | 50 | -7 | 7 | n.a. | n.a. |
| 13 | 45 | 50 | -5 | 5 | n.a. | n.a. |
| 14 | 45 | 50 | -5 | 5 | n.a. | n.a. |
| 15 | 48 | 50 | -2 | 2 | n.a. | n.a. |
| 16 | 49 | 50 | -1 | 1 | n.a. | n.a. |
| 17 | 52 | 50 | 2 | 2 | n.a. | n.a. |
| 18 | 53 | 50 | 3 | 3 | n.a. | n.a. |
| 19 | 55 | 50 | 5 | 5 | n.a. | n.a. |
| 20 | 52 | 50 | 2 | 2 | n.a. | n.a. |
| 21 | 51 | 50 | 1 | 1 | n.a. | n.a. |
| 22 | 49 | 50 | -1 | 1 | n.a. | n.a. |
| 23 | 48 | 50 | -2 | 2 | n.a. | n.a. |
| 24 | 46 | 50 | -4 | 4 | n.a. | n.a. |
| 25 | 49 | 50 | -1 | 1 | n.a. | n.a. |
| 26 | 51 | 50 | 1 | 1 | n.a. | n.a. |
| 27 | 52 | 50 | 2 | 2 | n.a. | n.a. |
| 28 | 51 | 50 | 1 | 1 | n.a. | n.a. |
| 29 | 51 | 50 | 1 | 1 | n.a. | n.a. |
| 30 | 48 | 50 | -2 | 2 | n.a. | n.a. |
| 31 | 45 | 50 | -5 | 5 | n.a. | n.a. |
| 32 | 46 | 50 | -4 | 4 | 2.75 | 1 |
| 33 | 51 | 50 | 1 | 1 | 2.75 | 1 |
| 34 | 54 | 50 | 4 | 4 | 2.8125 | 1 |
| 35 | 54 | 50 | 4 | 4 | 2.8125 | 1 |
| 36 | 52 | 50 | 2 | 2 | 2.71875 | 1 |
| 37 | 52 | 50 | 2 | 2 | 2.75 | 1 |
| 38 | 51 | 50 | 1 | 1 | 2.625 | 1 |
| 39 | 49 | 50 | -1 | 1 | 2.5625 | 1 |

FIG. 6A

Set Points at E1 = -5 and E2 = 5.5

| Amplitude Alarm Settings | | Derived Rate-Related Alarm Value: | |
|---|---|---|---|
| E1 | -5 | ET | 2.625 |
| E2 | 5.5 | | |

| | Empirical Values: | | | Calculated Values: | | |
|---|---|---|---|---|---|---|
| Time | Actual P | Set Point (SP) | Deviation from SP | Absolute Value of deviation | 32-Bit Summation | Alarm 2 (1=Yes) |
| 0 | 51 | 50 | 1 | 1 | n.a. | n.a. |
| 1 | 52 | 50 | 2 | 2 | n.a. | n.a. |
| 2 | 54 | 50 | 4 | 4 | n.a. | n.a. |
| 3 | 55 | 50 | 5 | 5 | n.a. | n.a. |
| 4 | 49 | 50 | -1 | 1 | n.a. | n.a. |
| 5 | 45 | 50 | -5 | 5 | n.a. | n.a. |
| 6 | 47 | 50 | -3 | 3 | n.a. | n.a. |
| 7 | 49 | 50 | -1 | 1 | n.a. | n.a. |
| 8 | 51 | 50 | 1 | 1 | n.a. | n.a. |
| 9 | 53 | 50 | 3 | 3 | n.a. | n.a. |
| 10 | 50 | 50 | 0 | 0 | n.a. | n.a. |
| 11 | 45 | 50 | -5 | 5 | n.a. | n.a. |
| 12 | 43 | 50 | -7 | 7 | n.a. | n.a. |
| 13 | 45 | 50 | -5 | 5 | n.a. | n.a. |
| 14 | 45 | 50 | -5 | 5 | n.a. | n.a. |
| 15 | 48 | 50 | -2 | 2 | n.a. | n.a. |
| 16 | 49 | 50 | -1 | 1 | n.a. | n.a. |
| 17 | 52 | 50 | 2 | 2 | n.a. | n.a. |
| 18 | 53 | 50 | 3 | 3 | n.a. | n.a. |
| 19 | 55 | 50 | 5 | 5 | n.a. | n.a. |
| 20 | 52 | 50 | 2 | 2 | n.a. | n.a. |
| 21 | 51 | 50 | 1 | 1 | n.a. | n.a. |
| 22 | 49 | 50 | -1 | 1 | n.a. | n.a. |
| 23 | 48 | 50 | -2 | 2 | n.a. | n.a. |
| 24 | 46 | 50 | -4 | 4 | n.a. | n.a. |
| 25 | 49 | 50 | -1 | 1 | n.a. | n.a. |
| 26 | 51 | 50 | 1 | 1 | n.a. | n.a. |
| 27 | 52 | 50 | 2 | 2 | n.a. | n.a. |
| 28 | 51 | 50 | 1 | 1 | n.a. | n.a. |
| 29 | 51 | 50 | 1 | 1 | n.a. | n.a. |
| 30 | 48 | 50 | -2 | 2 | n.a. | n.a. |
| 31 | 45 | 50 | -5 | 5 | n.a. | n.a. |
| 32 | 46 | 50 | -4 | 4 | 2.75 | 1 |
| 33 | 51 | 50 | 1 | 1 | 2.75 | 1 |
| 34 | 54 | 50 | 4 | 4 | 2.8125 | 1 |
| 35 | 54 | 50 | 4 | 4 | 2.8125 | 1 |
| 36 | 52 | 50 | 2 | 2 | 2.71875 | 1 |
| 37 | 52 | 50 | 2 | 2 | 2.75 | 1 |
| 38 | 51 | 50 | 1 | 1 | 2.625 | 0 |
| 39 | 49 | 50 | -1 | 1 | 2.5625 | 0 |

*FIG. 6C*

MONITORING AND CONTROL FOR A LARYNGEAL MASK AIRWAY DEVICE

BACKGROUND OF THE INVENTION

This application is a continuation-in-part of International application PCT/GB98/03849, filed Dec. 21, 1998, and with a claim of priority from original UK application No. 9727367.6, filed Dec. 24, 1997.

This invention relates to apparatus useful for controlling and/or monitoring the inflation pressure within a laryngeal mask airway (LMA) device and to a method and means for monitoring a patient's welfare by way of fluctuations in that inflation pressure.

LMA devices are now well known and are in widespread use in patient care, both during and after surgical procedures and during procedures that involve maintaining a clear airway. Such devices and their construction and use are described in various patent publications, for example, British Patent No. 2,205,499 and U.S. Pat. Nos. 4,509,514; 5,303,697; 5,241,956; and 5,282,464.

That such LMA devices are well accepted tools in patient care is borne out by simple statistics. For example, it is estimated that such devices are used in approximately 50 percent of all operative procedures requiring the use of general anaesthetic in the UK, and their use is becoming increasingly accepted elsewhere in Europe and in the USA.

Basically, an LMA device comprises an airway tube that is sized and curved for general conformance with a patient's airway; the airway tube extends from a proximal end that is external to the patient, to a distal end that carries mask structure in the form of a bowl or backing plate which faces and covers the patient's laryngeal inlet and which is continuously surrounded by a flexible ring or cuff that is selectively inflatable for resiliently sealed conformance to body structure around the laryngeal inlet. In use, the LMA is first fully deflated to aid its insertion and is then passed through the patient's mouth and throat into its correct position, with the mask over the laryngeal opening. The inflatable cuff surrounding the mask structure is then inflated to form a seal between the mask and the laryngeal opening. The air pressure with which the cuff is inflated forces the rear of the bowl of the mask against firm tissues at the back of the throat to maintain the device in place and to retain the seal. In this way, the device forms an open airway through which the patient's lungs can be ventilated.

Such LMA devices have proved to be both sturdy in construction and relatively straightforward to use, even by paramedics after the necessary training; however, if a mask is wrongly inserted, a reliable airway is not in fact formed and the patient's lungs are not then properly ventilated. In addition, the soft compliant silicone material of the cuff has been known to absorb nitrous oxide from anaesthetic gas mixture thereby increasing the pressure within the cuff, and the cuff itself may occasionally develop leakage causing its internal pressure to decrease. Also, it has been found that too high an inflation pressure will cause the cuff to restrict the blood supply to the mucosa overlying the muscles around the laryngeal inlet, and prolonged use of an LMA device in such circumstances can lead to tissue necrosis.

It has recently been proposed to monitor a patient's level of consciousness by means of a device capable of detecting and analyzing cerebral activity, in an attempt to avoid awareness during surgery; however, the equipment required for such monitoring is complex in operation and costly to manufacture. It has also been proposed to use automatic equipment to monitor intra-cuff pressure in a high-volume, low-pressure cuff associated with an endotracheal tube (EDT). And it has been reported that such an EDT device is able to measure and regulate intra-cuff pressure, to a tolerance of ±3-mm mercury.

We have observed that muscle tension (tone) in the lower throat (hypopharynx) bears a relationship to the patient's apparent response to painful stimuli; thus, it is possible to gain information on the patient's anaesthetic depth by monitoring muscle tone in the hypopharynx. And we have found that very small changes in that muscle tone are reflected through the LMA cuff and are further reflected through the shared air volume and that such pressure feedback readings can be utilized to both automatically adjust the inflation pressure of the LMA cuff and also to detect changes in the muscle tone in the hypopharynx. Of course, the detection of such changes is most preferably made without causing patient duress, and to such end it has been observed that it is most beneficial to inflate the cuff to pressures not much higher than 60-cm H2O; for example, 50-cm H2O, and generally in the range 25-cm H2O to 100-cm H2O. The acceptability of utilizing pressures above 60-cm H2O has been observed to cause patient throat irritation, especially in procedures of longer duration, and may risk damage to such tissue.

BRIEF STATEMENT OF THE INVENTION

The present invention has as its overall object to provide apparatus which is capable (a) of monitoring with fine sensitivity, for example 0.0625-cm H2O, the pressure within the cuff of an LMA device that has been properly installed within a patient's airway; and (b) of maintaining a preset inflation pressure within narrow tolerances, for example ±0.5-cm H2O.

It is also an object of the invention to provide apparatus which can be pre-programmed to recognize a variety of different patterns of pressure variation within the cuff of the LMA device and if necessary, to produce an appropriate range of different warnings to the operator in response to those patterns, and to be responsive to anomalous operating conditions threatening the integrity of the LMA device.

It is a specific object to provide monitoring apparatus of the character indicated, wherein, for the case of a patient who has been anaesthetized for surgery, the monitoring of LMA inflation pressure in the course of the surgery can include such automated analysis of LMA inflation pressure variation as to warn the operator that the patient has just exhibited an anomaly indicative of an incipient stage of awakening, thereby alerting the anaesthetist or anaesthesiologist (which are terms hereinafter used interchangeably) that the patient is in immediate need of further anaesthetic.

A further object is to provide apparatus which meets the foregoing objects, is relatively inexpensive to manufacture, is straightforward to set-up, and is reliable to operate and maintain.

A still further object is to achieve the foregoing pressure regulation without resort to utilization of some other form of system whose components would introduce an additional time constant or hysteresis effect on pressure monitoring functionality; such as would be caused by an accumulator-type system that is reliant upon a pumped or otherwise elevated pressure reservoir to replenish device operating pressure.

The invention seeks also to provide a method for maintaining a predetermined pressure in an LMA device and a method for monitoring pressure changes within the LMA device to detect changes in the patient's condition and to control the administration of anaesthetic and/or muscle relaxant.

A preferred embodiment of the invention meets the foregoing objects using apparatus for automatically controlling pressure in a laryngeal-mask airway device that has been installed in a patient, wherein the LMA device includes means that is inflatable to a predetermined level of pressure to establish sealed communication between the interior of the device and the patient's laryngeal inlet, said apparatus comprising:

(a) syringe means having a piston displaceable in an elongate cylinder with an outlet connection for supply of inflation air to the inflatable means;

(b) reversibly operable drive means for reversibly displacing the piston relative to the cylinder, thereby selectively displacing air to or from the inflatable means;

(c) control means including (i) pressure-responsive means connected for response to instantaneous pressure at the outlet connection, (ii) adjustable means for selecting a set-point value of inflation pressure, (iii) comparator means connected for response to a selected set-point value, for providing an electrical-output signal representative of the difference between instantaneous pressure and the selected set-point value; and (d) means connecting the electrical-output signal for operation of the drive means to displace the piston relative to the cylinder in the directional polarity to reduce to zero or near-zero the electrical-output signal provided by the comparator means.

Preferably, the reversibly operable drive means comprises an electric motor coupled for reversible drive of a lead-screw and nut means threaded to the lead screw, the nut means being longitudinally guided and keyed against rotation and connected for direct longitudinal displacement of the piston in the cylinder.

The preferred electric motor is a stepper motor driven in the open loop mode and which operates without slip or hysteresis lag/error. The direction and speed of the motor rotation are dependent upon the sequence and frequency of the phase of applied excitation.

More specifically, the reversibly operable drive means comprises such a stepping motor, in which the pressure-responsive means produces a first digital-signal output, in which the set-point value is in the form of a second digital-signal output, and in which the comparator means includes a microprocessor programmed to supply digital-control signals for operation of the motor.

Advantageously, a first normally closed solenoid valve is connected to the outlet connection of the syringe means for interposition between the outlet connection and the inflatable means, the solenoid of the valve having electrical connection to the control means whereby to actuate the valve to open condition for at least the time duration of the electrical-output signal and as long as the electrical-output signal is other than zero. A second normally closed solenoid valve is connected to the outlet connection of the syringe means; when actuated to open condition, this second valve provides syringe access to ambient air, for adding to or dumping system air, while the first solenoid valve is in closed condition.

Preferably, the cylinder has a ported but otherwise closed longitudinal end; and each of the two normally closed solenoid valves is connected to serve the ported end of the cylinder. The first normally closed solenoid valve is also connected to the inflatable means of the LMA and is actuable to interchange air between the inflatable means and the cylinder pursuant to the direction of displacement of the piston; and the second normally closed solenoid valve is actuable, as described above, to admit ambient air to the cylinder or to expel air from the cylinder, depending upon the direction of displacement of the piston. First limit-switch means produces an electrical signal for a sensed condition of piston advance into a predetermined limiting proximity to the closed end, and means including a microprocessor is responsive to the signal of sensed piston proximity, the microprocessor being programmed (i) to foreclose operation of the drive means and to return the first solenoid valve to its normally closed position, then (ii) to actuate the second solenoid valve to open condition while operating the drive means for a predetermined stroke in reverse, thus inducing a fresh charge of ambient air into the cylinder pursuant to the predetermined stroke in reverse, and (iii) deactivating the second solenoid valve and enabling the comparator means to reestablish the set-point value of pressure within the cylinder before reactivating the first solenoid valve and returning the comparator means to its function of regulating LMA-inflation pressure to its set-point value.

In a further microprocessor-controlled feature of the currently preferred system, as for a patient who has been anaesthetized and is undergoing surgery, mask-inflation pressure is continuously monitored. The instantaneously observed mask-inflation pressure is monitored for possible traverse of predetermined upper and/or lower threshold limits of "normal" regulation; and, upon observed-pressure traverse of one of these limits, a first alarm signal is issued with an audible warning, it being interpreted that, even though still asleep and under sedation, the patient has involuntarily betrayed an indication of hypopharynx/larynx muscle contraction, with accompanying transient local compression of the patient's inflated LMA. Further automated monitoring is concurrently performed to determine whether any rate-related conditions occur, beyond a predetermined magnitude of an evaluated criterion. Such rate-related occurrences are further described below and are determined by continuous review of analyses performed on a gated sequence of several successive readings that are stored-within the system; and the output of such analyses is continually displayed at the system monitor. This rate-related analysis of observed inflation pressure provides further indication of the patient's incipient and prospective awakening process and provides verification of first alarm, further alerting the anaesthesiologist with visual warning to "check anaesthesia".

BRIEF DESCRIPTION OF THE DRAWINGS

Apparatus and methods of the present invention will be described in greater detail by way of example and with reference to the accompanying drawings, in which:

FIG. 3 comprises separate sheets labeled FIG. 3 (Part A) and FIG. 3 (Part B), and is a more schematic diagram of control means including a comparator component and motor-control circuit for the system of FIG. 2, wherein measured pressure is evaluated against a set-point SP for determining drive for an air-displacing piston and is further evaluated against thresholds for determining status of pain-stimulus alarms; the phantom line 3A of FIG. 3 (Part A), and the phantom line 3B of FIG. 3 (Part B) represent one and the same plane at which FIG. 3 (Parts 3A/3B) are connected to complete FIG. 3;

FIG. 6A and FIG. 6C are tables detailing typical calculations performed on sampled test data, comparing these values to set-point, and performing rate-related alarm calculation for each sample;

DETAILED DESCRIPTION

A. Mechanical Construction and Operation

Figure 1:
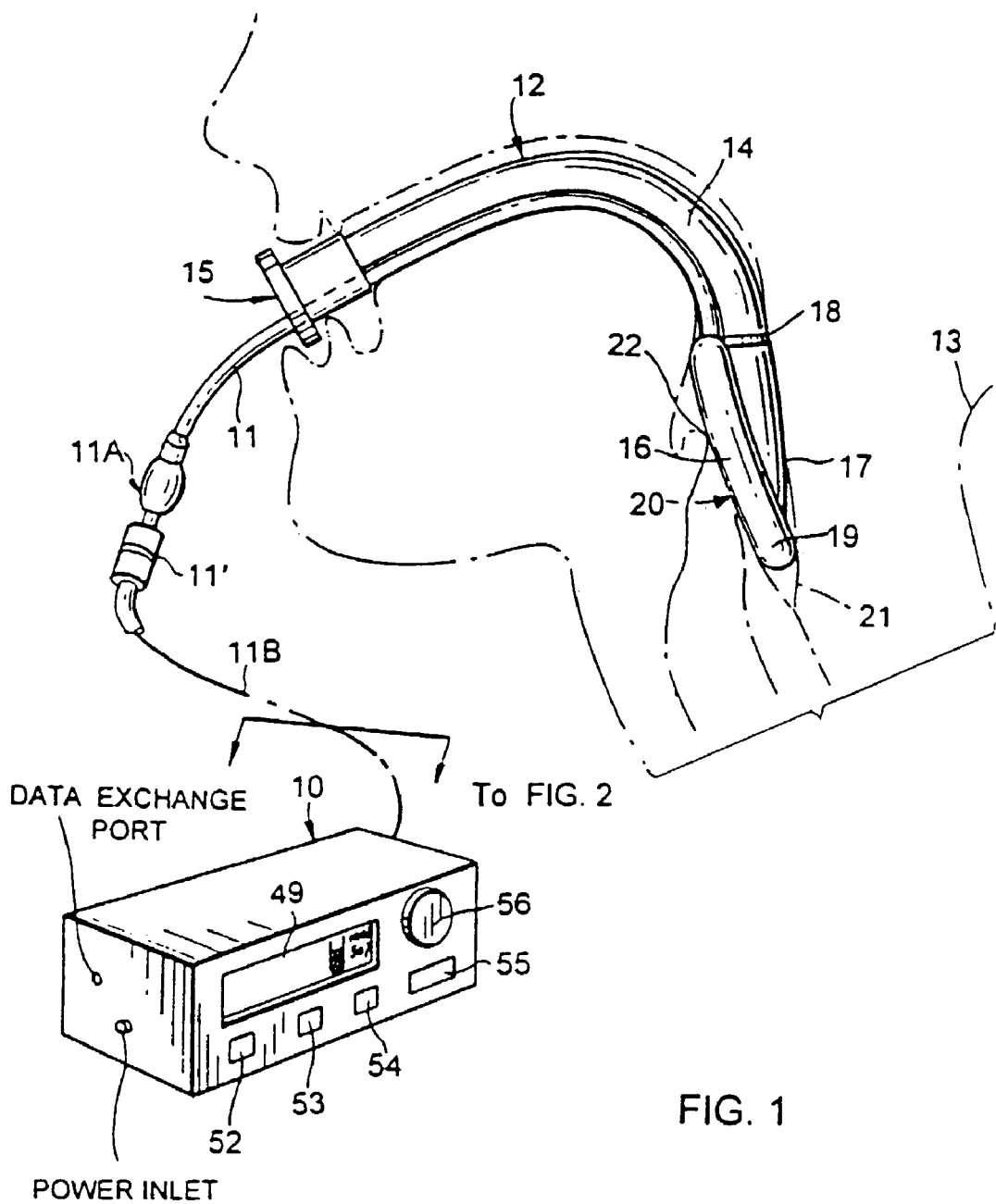
FIG. 1 is an illustration of a control/monitor system of the invention, coupled to an LMA device installed in a patient.
Figure 2:
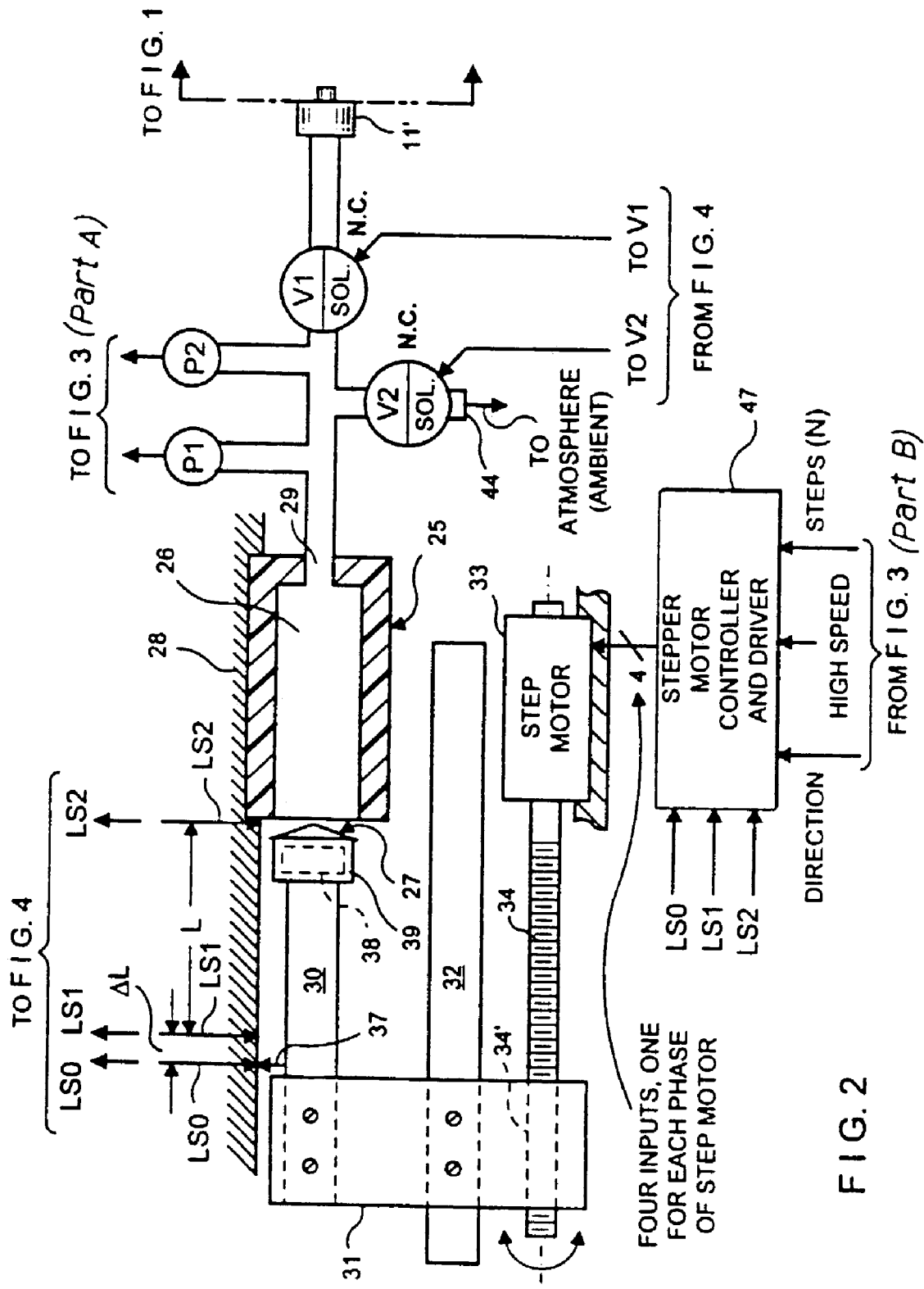
FIG. 2 is a diagram of mechanical components of FIG. 1, with schematic indication of motor-control components.

In FIG. 1, the monitoring system or device of FIG. 2 is shown at 10 with various control buttons including a system start/stop button 52, a "regulation" start/stop button 53, an alarm-reset button 54, an "ENTER" button 55, and a rotary knob 56 for selection, inter alia, of set-point or threshold.

The monitoring system 10 has an outlet connection to the flexible inflation/deflation air-supply line 11 of an LMA device 12 installed in a patient 13. The LMA device 12 is seen to comprise an airway tube 14 with proximal-end means 15 for external accommodation of ventilating or anaesthetizing supply to the patient's lungs via mask structure 16 having a backing plate 17 connected at 18 to the distal end of tube 14, the backing plate being peripherally surrounded by an inflatable/deflatable ring or cuff 19 of resiliently flexible material; cuff 19 is shown in inflated condition, in peripherally sealed relation to body structure surrounding the patient's laryngeal inlet 20, and in distally located relation to the patient's aesophageal inlet 21 (the hypopharynx). Internal structure of the mask will be understood to include known means (not shown) to prevent the patient's epiglottis 22 from interfering with air or anaesthetizing flow through the mask, in either direction, between tube 14 and the patient's laryngeal inlet 20.

Conventionally, the inflatable/deflatable ring or cuff 19 of an LMA device is operated manually by a hand-held syringe (not shown) that is detachably connected to check-valve means 11A forming an outer end of line 11 of the LMA; when the syringe is detached, the check-valve means 11A is operative to retain the currently inflated or deflated state of the LMA. By experience, the anaesthetist will know roughly to what pressurize the cuff can safely be inflated once the LMA has been properly installed in the patient. Although the control system can be utilized to inflate the cuff after it is installed in the patient, especially with the smaller cuff sizes, the above described manual procedure of inflation is recommended prior to connecting the LMA inflation/deflation line 11 to the control system of FIG. 2.

In FIG. 2, an air-control port 11' will be understood to include suitable means for detachable connection to the inflation/deflation air line 11 of FIG. 1; and an elongate flexible connection or extension line 11B has (i) a system-connector end (not shown) that is detachably connected to control port 11', and (ii) an LMA-connector end that is compatibly connected to so coact with the connector end of the check-valve means 11A as to maintain lines 11/11B as a continuously open passage of system communication with inflatable means 19 of the LMA. Air-displacement means may comprise syringe means in the form of a solid body 25 of low-friction material such as PTFE (Teflon) with a cylindrical bore 26 having an open (or tail) end for coaction with piston means 27; but it is currently preferred that body 25 be of stronger material such as aluminum, with a lubricant and/or anti-friction coating in the bore 26 of the cylinder for sealed engagement with a resilient O-ring or lip carried by and effectively forming part of piston means 27. Body 25 is fixed to a frame member 28 and extends longitudinally to a closed (or head) end having a port connection 29 to a direct line to the LMA inflation/deflation connection means 11'; in this direct line, a first normally closed solenoid valve V1 must be actuated to open condition if inflation air is to pass in either direction between cylinder 26 and the inflatable/deflatable means 19 of the LMA.

Piston 27 is rigidly mounted to or formed with the head end of a longitudinal rod 30, the tail end of which is clamped to a slide block 31. Block 31 establishes a rigid lateral-offset arm for longitudinally stabilized guidance at 32 and for reversibly driven longitudinal displacement by frame-based electrical stepper motor means 33 and its lead-screw output shaft 34; shaft 34 has threaded engagement to a nut-like bore 34' in the rigid lateral-offset arm of slide block 31, and preferably the threaded bore 34' is formed in a body of PTFE that is secured to slide block 31. The guide means 32 will be understood to be a schematic designation for a commercial longitudinal "linear-bearing" assembly (widely known and available under the name or mark "ROLLON") wherein an elongate first raceway element is fixed to a frame member, wherein an elongate second raceway element is fixed to the slide block 31, and wherein antifriction elements, such as bearing balls, ride and space the raceways of the respective raceway elements. The described arrangement of longitudinal support and guidance afforded by means 32 will be seen as establishing precise longitudinal displaceability of piston 27 along the central longitudinal axis of the cylindrical bore 26, with block 31 and piston 27 effectively keyed against rotation about the lead screw.

Motor means 33 is of a stepping variety wherein a precise directional control is effected via variance of the relative excitation of each of-four input terminals of the motor. The amount of shaft 34 rotation (and thus of piston 27 displacement) is controlled by motor controller and driver means 47, as shown in FIG. 2.

Legends in FIG. 2 indicate an overall length L of piston 27 travel in bore 26, for purposes of delivering inflation air from bore 26 to the inflatable/deflatable ring or cuff 19 of the LMA, as long as solenoid valve V1 remains actuated to open condition; this same length can also be available for a retraction stroke of piston 27, wherein a controlled quantity of inflation air may be extracted from cuff 16. Fixedly mounted limit switches LS1 and LS2 are schematically indicated by arrow marks in FIG. 2, to suggest a stop and/or reversing device at each of the longitudinal limits of the overall length L of piston travel. However, as shown in FIG.

2, piston 27 is at offset ΔL outside of the cylindrical bore, wherein the arrow designated LSO identifies the point at which a coacting lug or other switch-actuating device 37 carried by piston rod 30 coacts with limit switch LSO to electrically or otherwise signal achievement of the piston-retracted position shown, with concomitant termination of drive pulses from driver circuit in FIG. 3; suitably and preferably, each of the limit switches is an optical device, relying on the lug or other actuating device 37 to be opaque and therefore able to cut or interrupt a light beam, from a source to a photocell, at each of the respective locations at which limit switch action is to occur.

As further shown in FIG. 2, the head end of piston rod 30 has a radial flange formation 38, circumferentially shrouded by a resilient cap 39, having an undercut bore which readily snaps into resiliently retained engagement to the flange formation 38, as when servicing the apparatus by replacing a used cap 39 with a new cap 39; it will be understood that the lip relied upon for sealed engagement to bore 26 may be an integral formation of cap 39.

Some pressure-regulating operations can have the effect of causing interference with the sensing of pressure changes reflecting patient muscle reflex. The system of the invention has been designed to minimize such interference through its design concept as an essentially closed-volume system, wherein adjustments for cuff 19 pressure deviation are made by increments of displacement within a shared volume of air, as between (i) the volume ahead of the piston 26 and within the head end of the cylinder and (ii) the volume in the cuff 19. This is superior to systems that regulate pressure by using an accumulator or reservoir of elevated pressure to compensate for cuff pressure changes either by introducing air from such an accumulator or by voiding air to atmosphere.

The inherent increase in system stability resulting from use of the shared-volume concept that is utilized by the system of the invention allows a high degree of accuracy without associated system hunting or over-adjustment. Specifically, approximately 0.0005 ml (0.5 micro-liters) of air is moved with each step taken by stepper motor 33. Such performance is presently not available for a pressurized accumulator-type system.

Further elements of the apparatus of FIG. 2 comprise first P1 and second P2 pressure-monitoring transducers. These pressure transducers, which indicate the overall pressure in the device, are connected to redundantly monitor air pressure in the line between cylinder-outlet port 29 and the normally closed first solenoid valve V1.

A second normally closed solenoid valve V2 is shown connected to the air line between cylinder port 29 and the first solenoid valve V1. When actuated to open condition, valve V2 establishes a path from its open-air end 44 to the air line from cylinder port 29 to the first solenoid valve, so that, with valve V1 in its closed unactuated condition and with valve V2 actuated to its open condition, a right-to-left displacement of piston 27 in cylindrical bore 26 will induce an inflow of fresh (ambient) air into the described system. Similarly, with the two valves V1 and V2 in the same condition (of V2 actuated and of V1 in its normally closed condition), a left-to-right displacement of piston 27 in bore 26 will discharge excess air or gas from the system.

Also, and analogously, with valve V2 in its normally closed condition and with valve V1 actuated to its open condition, a right-to-left displacement of piston 27 will draw inflation air from (and thus deflate) means 19 of the LMA. And for the same conditions of valve V2 unactuated and of valve V1 actuated, a left-to-right displacement of piston 27 will supply inflation air to means 19 of the LMA. Control signals necessary for actuation of valves V1 and V2 are provided by separate outputs that are derived from basic program-sequencing signals from a separate microprocessor means of a controller 60 for start-up, centering, and reset.

A.1. System Start-Up

Figure 4:
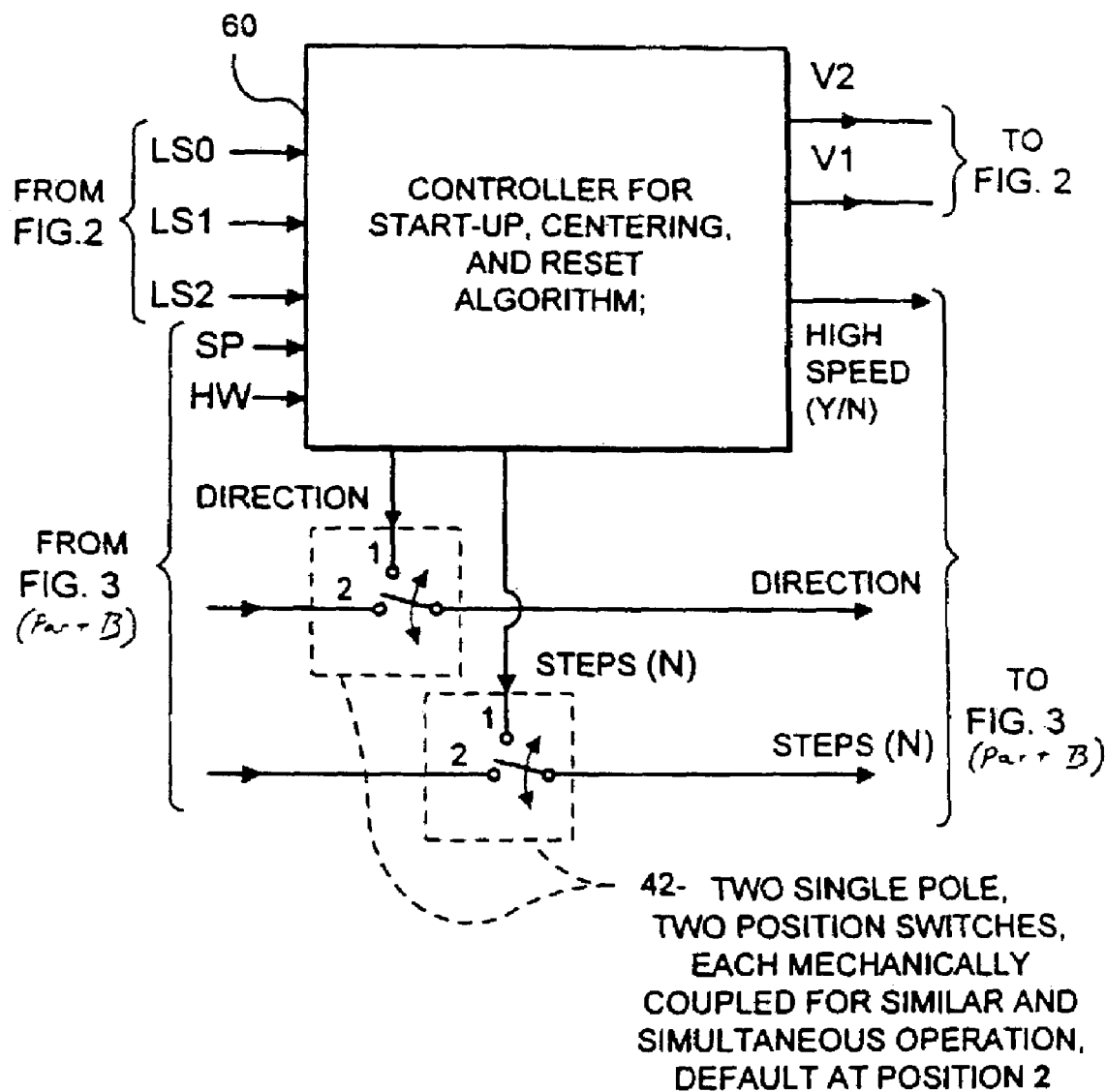
FIG. 4 is a schematic of means by which the system can transfer between start-up, centering, and reset circuitry.

For purposes of system start-up and centering operations, the control circuit of FIG. 3 is bypassed and the inputs to stepper motor controller and driver 47 are controlled by the controller 60 for start-up, centering, and reset. As shown in FIG. 4, the bypass of the FIG. 3 control circuit is accomplished by the operation of two single-pole, two-position switches 42. Such operation of switches 42 will occur when the unit is first powered up, at which point a start-up sequence is initiated. The operation of stepper motor 33 is controlled during start-up sequence by controller (60) for start-up, centering, and reset.

Before proceeding with illustrative description of automated operation of the regulating system of FIGS. 1 and 2, it is noted that for practical purposes, the system must compatibly operate with suitably sized LMA's for patients of all ages, requiring ring 19 inflation volumes which will differ by as much as 10:1 between extremes. The sizes currently available for the anaesthetist's selection are as follows:

Size 1 (small infant), 4 cc maximum inflation volume.
Size 1.5 (larger infant), 6 cc maximum inflation volume.
Size 2.0 (small child), 10 cc maximum inflation volume.
Size 2.5 (larger child), 14 cc maximum inflation volume.
Size 3.0 (small adult), 20 cc maximum inflation volume.
Size 4.0 (average adult), 30 cc maximum inflation volume.
Size 5.0 (large adult), 40 cc maximum inflation volume.

It is currently preferred to design the displacement-volumetric capacity of the syringe bore 26 to be substantially 20 cc, between LS1 and LS2 operations at the respective extremes of piston displacement L in bore 26; for a bore 26 diameter of 24 mm, the displacement-volumetric capacity of 20 cc is realized by a full-stroke displacement L of about 45 mm, which can be taken as the illustratively useful displacement range of the system. Further illustratively, for a stepping motor 33 designed to require 1600 pulsed steps for a single revolution of its lead-screw 34, and for a lead-screw pitch (i.e., advance per turn) of 2 mm, the useful range L of piston 27 displacement involves 36,000 discretely pulsed step increments; for initial set-up purposes, a recommended "fast" repetition rate of pulsed steps at 5,000 Hz is to be applied to produce a piston-displacement speed of 6.25 mm/sec. For normal pressure-regulating displacements, a recommended "slow" repetition rate of pulsed steps at 500 Hz is to be applied to produce a piston-displacement speed of 0.625 mm/sec. It is explained below that any automatic pressure-regulating correction is preferably achieved by an increment of piston displacement, wherein the increment begins from the mid-point of the useful range L, so that the indicated regulating range of motor displacement is normally accomplished within the scope of 18,000 pulses to motor 33, thus enabling a volume displacement of at least 10 cc, in the LMA-inflating direction or in the LMA-deflating direction, as needed. For automated regulation of LMA inflation to set-point pressure, this range limitation is found to serve any of the above-noted LMA sizes, even though the range of inflation volumes is about 10:1.

It has been recommended above that the system of FIGS. 1 and 2 be connected (at 11') to the inflatable means 19 of the LMA only after having followed the conventional procedure of using a hand-held syringe (not shown) to evacuate means 19 for purposes of LMA insertion in a patient, and for then using the same syringe to effect an inflation which the operator knows from experience will establish a properly located seal of means 19 around the laryngeal inlet, and with distally contacting engagement with the hypopharynx.

The preferred method of initially inflating LMA ring 19 is for the anaesthetist to use syringe means. Whether or not the LMA inflation ring 19 is inflated manually, the system of FIGS. 1, 2 and 3 is adapted to quickly assume pressure-monitoring control of inflation ring 19 to the predetermined set point, which will be understood to present a desired pressure set-point value SP (e.g., 50-cm H2O) as part of the display 49. Although the LMA control system 10 is capable of performing the initial task of cuff inflation, such initial inflation by the system 10 may be practical only for cuffs of smaller volume capacity and is not presently preferred.

Thus, with pressure threshold set-point SP selected and established for the system of FIGS. 2 and 3, programmed operation will begin with the controller 60 (for start-up, centering, and reset) controlling the initial start-up sequence. The controller 60, as shown in FIG. 4, contains an algorithm that actuates valve V2 to open condition, leaving valve V1 in its unactuated (and therefore in its normally-closed) condition. Pulses are then sent at high speed (5,000 Hz) via stepper motor controller and driver 47, operating motor 33 to displace at high speed piston 27 from its retracted position, which is determined by lug 37 coaction with limit switch LS0. Piston 27 rapidly traverses the full range (L) of piston 27 travel in bore 26 in left-to-right motion. In the course of this traverse, lug 37 will actuate limit switch LS1, thereby initiating in the stepper motor controller and driver 47 a count of number of pulses that are required to drive the piston as a function of displacement L. The count is terminated only when lug 37 actuates limit switch LS2, at which point the full count is entered into memory of controller 60, and an automatic divide-by-two operation is effected, with its half-count value entered into memory of the controller 60 and also entered into memory of the stepper motor controller and driver 47. Thereafter the stepper motor controller and driver 47 will track each subsequent command that operates motor 33 to independently maintain an awareness of piston 27 position.

A signal is then sent by the controller 60 for travel to start in the opposite direction at the same high rate of speed until a pulse count is reached indicative that piston 27 has reached its mid-position (or "L/2"). Valve V2 is then deactivated, returning it to its normally-closed condition.

Both switches 42 in FIG. 4 then simultaneously transfer from the first ("1") position to the second ("2") position, thereby allowing a fuzzy-logic controller 46, shown in FIG. 3, to assume control of motor 33. The fuzzy-logic controller 46 will operate in accordance with logic rules set forth below in Table 1, providing the signal necessary for piston 27 to continue its travel in the left-to-right direction until pressure generated at the head end of the cylinder 26 equals a preprogrammed check-point pressure, typically 20-cm H2O; and once such value has been attained, for reasons explained in the following section, piston 27 will be further actuated to continue its travel until the set-point value SP has been attained. The controller 60 will then actuate valve V1, transferring V1 to open condition.

Should the controller 60 (for start-up, centering, and reset) fail to receive indication that the preprogrammed check-point pressure has been attained within a predetermined number of stepper motor (33) steps (e.g., the prepro-grammed check-point pressure to be attained prior to travel of the number of steps required for piston 27 to traverse one-eighth (⅛) of displacement L), an audible and visual alarm will issue and the system will prohibit automatic system operation.

A.2 Failsafe Mode

A failsafe mode may be triggered during the course of regular system operation upon substantial deviation between the redundant pressure sensors. The pressure is redundantly sensed by pressure transducers P1 and P2, from which independently sensed pressure readings are continuously compared by a comparator means "A" 40. A hardware-error HW alarm will be generated when a difference other than substantially zero is detected between P1 and P2. This hardware-error alarm is issued in the form an audible and visual indication, alerting the anaesthesiologist to assume manual inflation control of the LMA. Then, a short period of time after issuing such hardware-error alarm, comparator means "A" 40 will go to failsafe mode, closing V1 and V2 in order to maintain the pressure within the LMA cuff.

B. Normal System Control

Fuzzy-logic controller operation is described by the logic rules set forth below in Table 1. The first two columns in Table 1 reflect the previous pressure and the current pressure, each as compared to SP. As noted in FIG. 3B, the delay time between the first and second columns is one-half (½) second. The last column in Table 1 reflects the command that will typically be sent by the fuzzy-logic controller 46 to motor controller 47. Because during normal operation the stepper motor 33 operates only at slow speed, the fuzzy command is sent in terms of direction and number (N) of steps. The described pressure-regulating process that is conducted by the fuzzy-logic controller preferably performs its task within a range of operation defined by a deadband of 0.5-cm H2O on each side of the set-point SP.

TABLE 1

Operation of Fuzzy Logic Controller 46

| Previous Actual Pressure in relation to Set Point | Current Actual Pressure in relation to Set Point | Decision in Steps (N) and Direction |
|---|---|---|
| High | High | High number of steps, reverse |
| Medium | High | High number of steps, reverse |
| High | Medium | Low number of steps, reverse |
| Medium | Medium | Minimal number of steps, bi-directional |
| Low | Medium | Low number of |
| Low | Low | High number of steps, forward |
| Medium | Low | High number of steps, forward |

C. Typical Waveform for an Anaesthetized Patient

Figure 5:
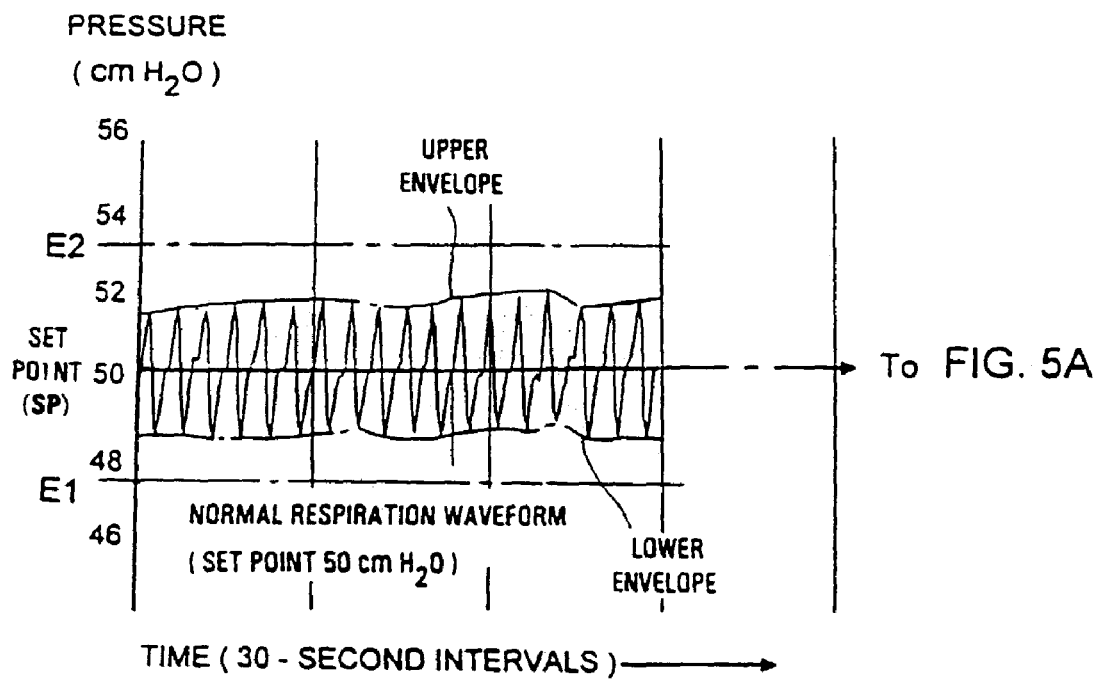
FIG. 5 is a graphical display of system-observed pressure variations as a function of time in the seal cuff of an LMA that is installed in a patient who has been anaesthetized and is undergoing surgery, but has, as yet, had no pain stimulus.

FIG. 5 illustrates a respiratory waveform which the system of the invention has used both to regulate pressure of the LMA cuff 19 and to monitor the LMA-inflation pressure. The patient in this example is under surgery and is being mechanically ventilated, i.e., the patient's ventilation is the result of positive pressure being exerted through airway tube 14, also referred to as intermittent positive-pressure ventilation, or "IPPV". FIG. 5 depicts the ability of the device of the invention to monitor oscillations (fluctuations) about the set-point SP (50-cm H2O in this example), wherein such oscillations occur at a rate of approximately twelve cycles per minute, which is typical of the respiratory cycle of a "normal" anaesthetized adult patients.

Figure 5A:
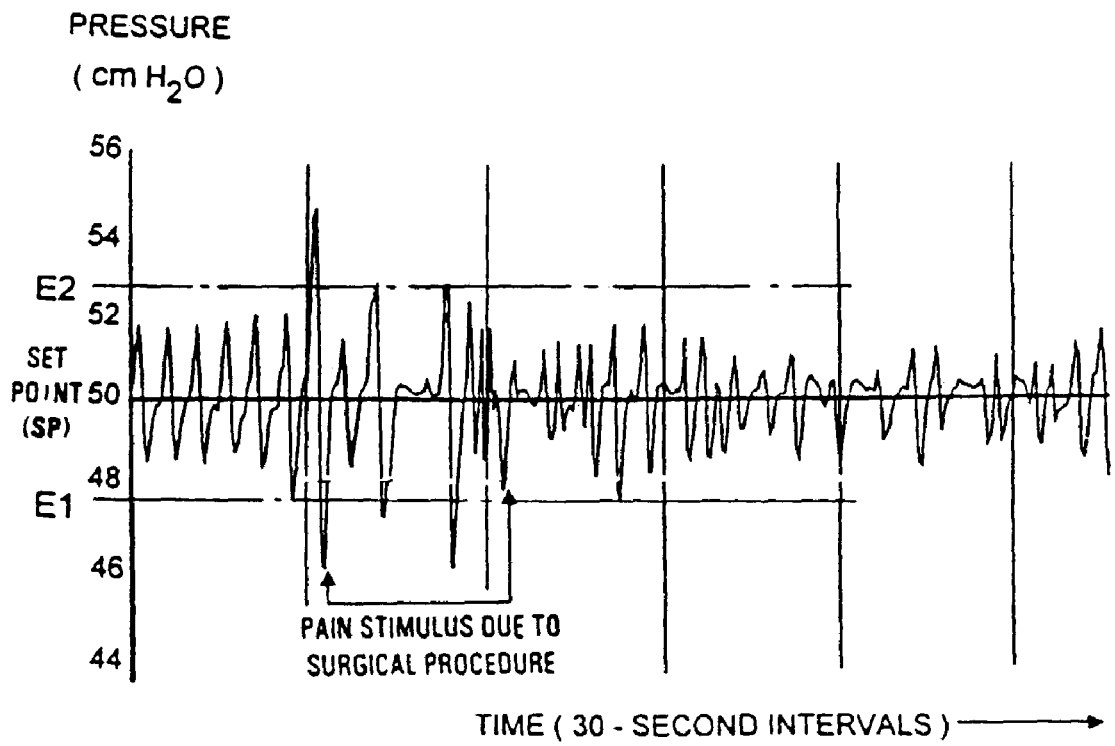
FIG. 5A is a graphical display as in FIG. 5, just before and following display of system response to an illustrative anomaly that reflects a pain stimulus.

It has been discovered that such respiratory flow, through airway tube 14, whether spontaneous or by IPPV, will have the effect of causing the LMA cuff 19 to undergo regular cycles of compression/expansion. One of the objects of the system of the invention is to measure the magnitude of both the compression/expansion cycles as well as to detect deviations from such compression/expansion cycles as can be determined to indicate pain stimuli. Although there is an overall expansion of the FIG. 5 signal envelope (as such is shown in FIG. 5 and which will be further explained below in the section on autoscaling), there are not as of yet any indicia of pain stimuli in FIG. 5. FIG. 5A provides an example of the patient experiencing a pain stimulus, which the system of the invention will detect and report via alarm procedures that are the subject of discussion below.

The graph of FIG. 5A is illustrative of competing forces at play, once disturbed by reaction to a pain stimulus of the character indicated. First of course, one is reminded that the system of the invention will have been in its normal "regulating" mode, doing what it can, based on its repeated sampling (at 0.5-second intervals) of measured pressure (e.g., P1) in relation to the set point SP and using this reading to determine and make the proper displacement of piston 27. The pattern of neuromuscular-derived pressure variations which follow a pain stimulus, and piston displacements that will be called for and may not be within the capacity of described mechanism to track, can therefore create a disturbed pattern of measured pressures while the regulating mode is attempting to reestablish itself. Still further, the normal regulating mode and the patient's neuromuscular system will be attempting to adapt to changed and changing conditions, as may result from the patient's neuromuscular response to a deepening ("rescuing") further dose of anaesthesia.

D. Monitoring Function

FIGS. 3, 5, and 5A, and the charts and tables FIGS. 6A, 6B, 6C, and 6D, serve for illustration of two automatic techniques whereby the device of FIGS. 1, 2, and 3 can alert the anaesthetist that, during the course of a surgical operation on an anaesthetized patient, the patient has given an early neuromuscular indication of a pain stimulus which the patient's current anaesthetized level has been unable to block, even though the patient is still sufficiently sedated to be unconscious or otherwise unaware of the pain stimulus. Such neuromuscular indication demonstrates to the attending anaesthetist that the patient is contracting muscles of his larynx and hypopharynx—a phenomenon indicative of an incipient stage of the patient's awakening process—with potentially serious consequences if the surgical procedure has not yet been completed.

Although it is known that patients under the effect of a general anaesthesia become insensitive to pain stimulus, such sensitivity has been discovered to be particularly active and observable at muscle systems surrounding the laryngeal inlet and the hypopharynx area. It has been further discovered that such activity of these muscle systems will vary with the depth of anaesthesia and can be observed by pressure fluctuations in an inflated LMA cuff 19 having resiliently loaded continuous contact with such muscle systems. Specifically, anomalous pressure readings in the output of pressure comparator "A" 40 are recognized by comparators "B" 57, "C" 58, and "D" 59 in FIG. 3 to develop output alarms A1 and A2. The inflated ring or cuff 19 of the installed LMA is thus the means of early detection of a localized neuromuscular response, which is deducible from a sudden reaction of the regulating function of the described system, as the same is seen to occur in the disturbed and irregular pattern of pressure excursions in FIG. 5A, wherein bracketing and legend identify a period of pain stimulus due to an event occurring during a surgical procedure.

Figure 7:
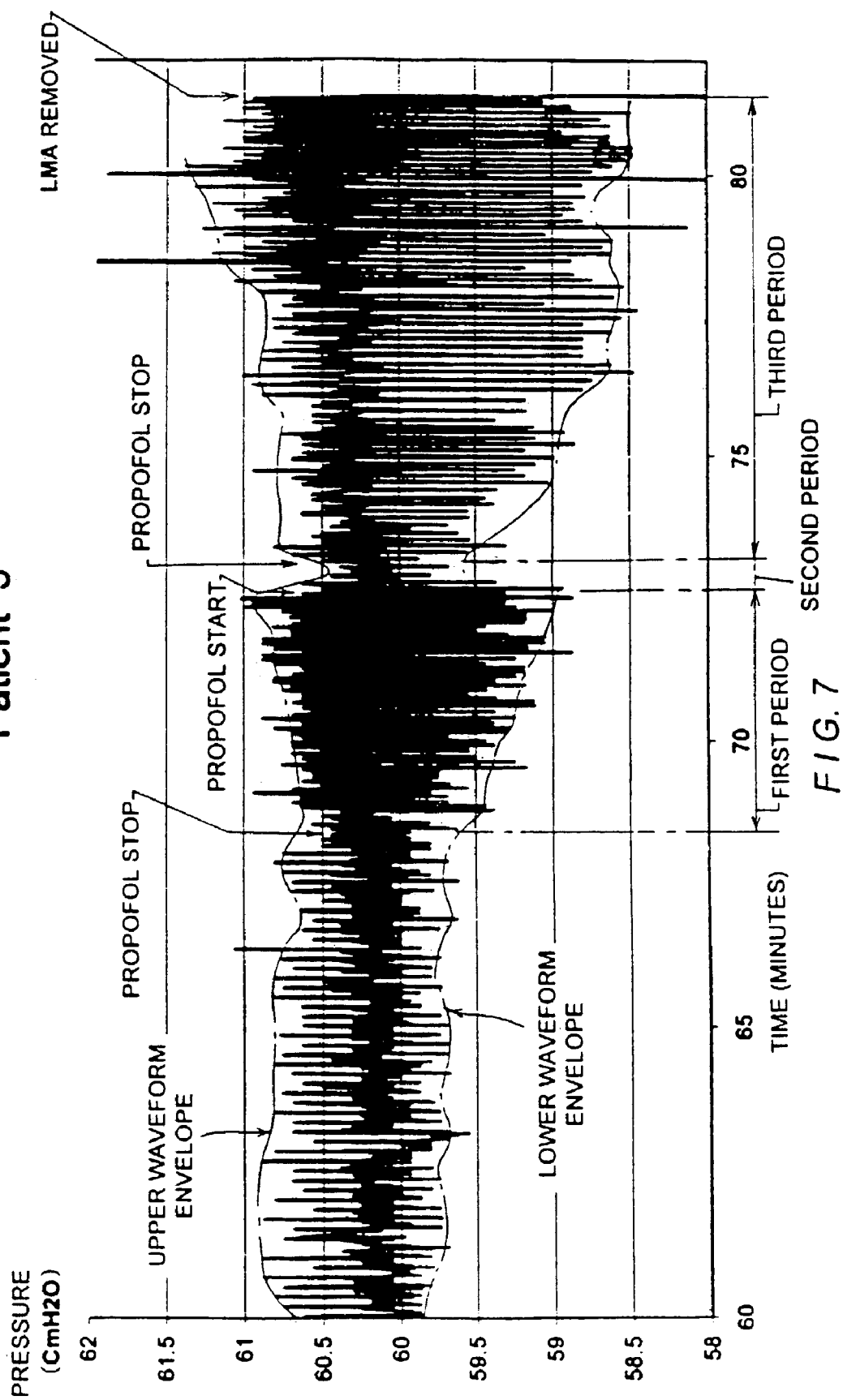
FIG. 7 is a display of observed empirical data obtained during the awakening sequence of a patient; such data providing an example of a pain-stimulus response that is revealed by analysis of the monitoring function of the system.

FIG. 7 displays empirical values of the varying pressure fluctuations that were observed to occur as the anaesthetist intentionally allowed the patient to partially revive from the depths of anaesthesia, it being understood that a chart similar to FIG. 7 was available in real time on display 49 during the course of the surgical procedure. The pressure changes are displayed on the ordinate in cm H2O, with the set-point SP having been selected at 60-cm H2O. FIG. 7 displays events that transpired toward the conclusion of a surgical procedure in which the patient, "Patient 5", was anaesthetized with a continuous feed of propofol, a common and popular anaesthetic.

Three specific time periods are recognizable in FIG. 7, and each of these intervals corresponds to the initiation of a variance in the amount of anaesthetic administered to Patient 5. In the first of these periods, beginning at time 68-minutes, the continuous administration of propofol was stopped. And in an ensuing remainder of the first period, a significant increase in activity of muscles in the larynx/pharynx area is readily observable in the region contacted by the LMA cuff 19.

Correlation of increased muscle activity (in the larynx/pharynx region) to the patient's depth of anaesthesia has been discovered to be of significant benefit in maintaining proper anaesthesia levels during the course of surgical and other proceedings. Use of the LMA device and monitoring apparatus provides means by which such observations can reliably be made with the additional benefit of hot subjecting the patient to further intrusive apparatus.

During the second period marked in FIG. 7, the beginning of which occurred at approximate time 72-minutes, the anaesthetist restarts the administration of propofol. The third period in FIG. 7, starts at approximate time 73-minutes, and identifies when the administration of propofol was again stopped, and the patient was allowed to fully awaken. Note that there are no further readings after approximate time 82-minutes, because the LMA was at that time removed from the patient's laryngeal area.

The events displayed in FIG. 7 provide clear evidence that the monitoring system of the invention functions at a level of sensitivity permitting detection of muscular activity indicative of the awakening sequence.

D.1 Automated Alarms

Two techniques recommended for automatic interpretation of the anomaly described in FIG. 5A are further described below. These alarms can be monitored by the anaesthetist for immediate or early recognition of the pressure anomaly that has been observed as a symptom caused by an early incipient stage of the patient's awakening process.

Both techniques rely upon the establishment of fluctuation boundaries (thresholds) on each side of the normal respiration waveform and the comparison of LMA (ring 19) pressure to such limits; these are shown as upper and lower thresholds E1 and E2 in FIGS. 5 and 5A and are referred to as the "check anaesthesia alarm window". As shown in FIG.

3, E1 and E2 are the values automatically compared to each pressure signal fluctuation for determination of the anaesthesia-level alarms, A1 and A2. The attending anaesthetist is able to individually select, i.e., to vary E1 and E2 via monitoring device 10. A1 is an instantaneous-type alarm, triggered whenever the respiration waveform deviates above or below the "check anaesthesia" alarm window that is framed by E1 and E2. The initial warning alarm A1 is triggered by any single deviation from the "check anaesthesia" alarm window. The A1 alarm will be presented to the anaesthesiologist in audible form. Once thus warned, the anaesthetist is alerted to make an immediate corrective response, as by increasing the strength of the anaesthetic being administered to the patient.

Figure 6B:
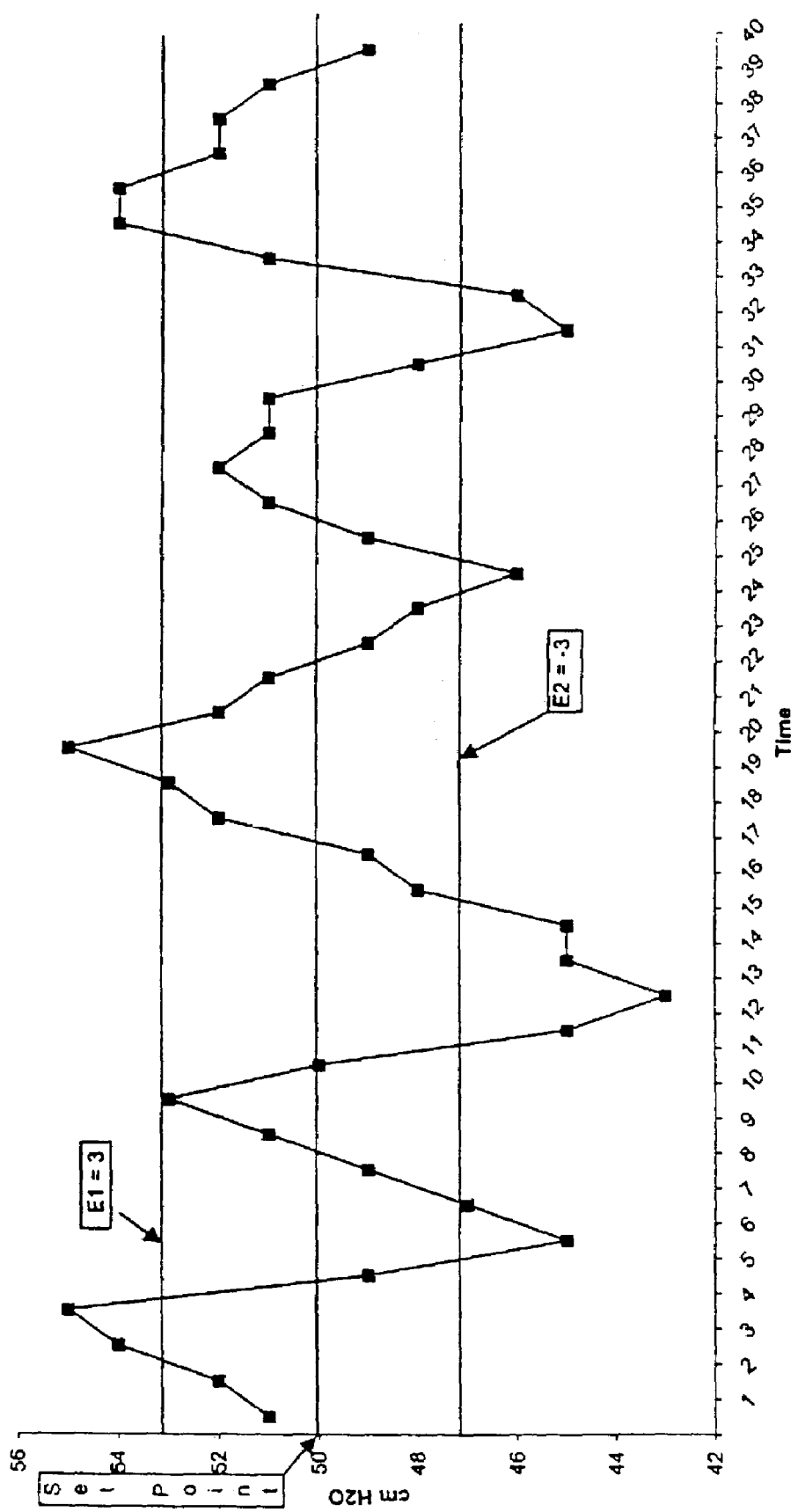
FIG. 6B and FIG. 6D are graphical representations of the values presented on FIG. 6A and FIG. 6C.
Figure 6D:
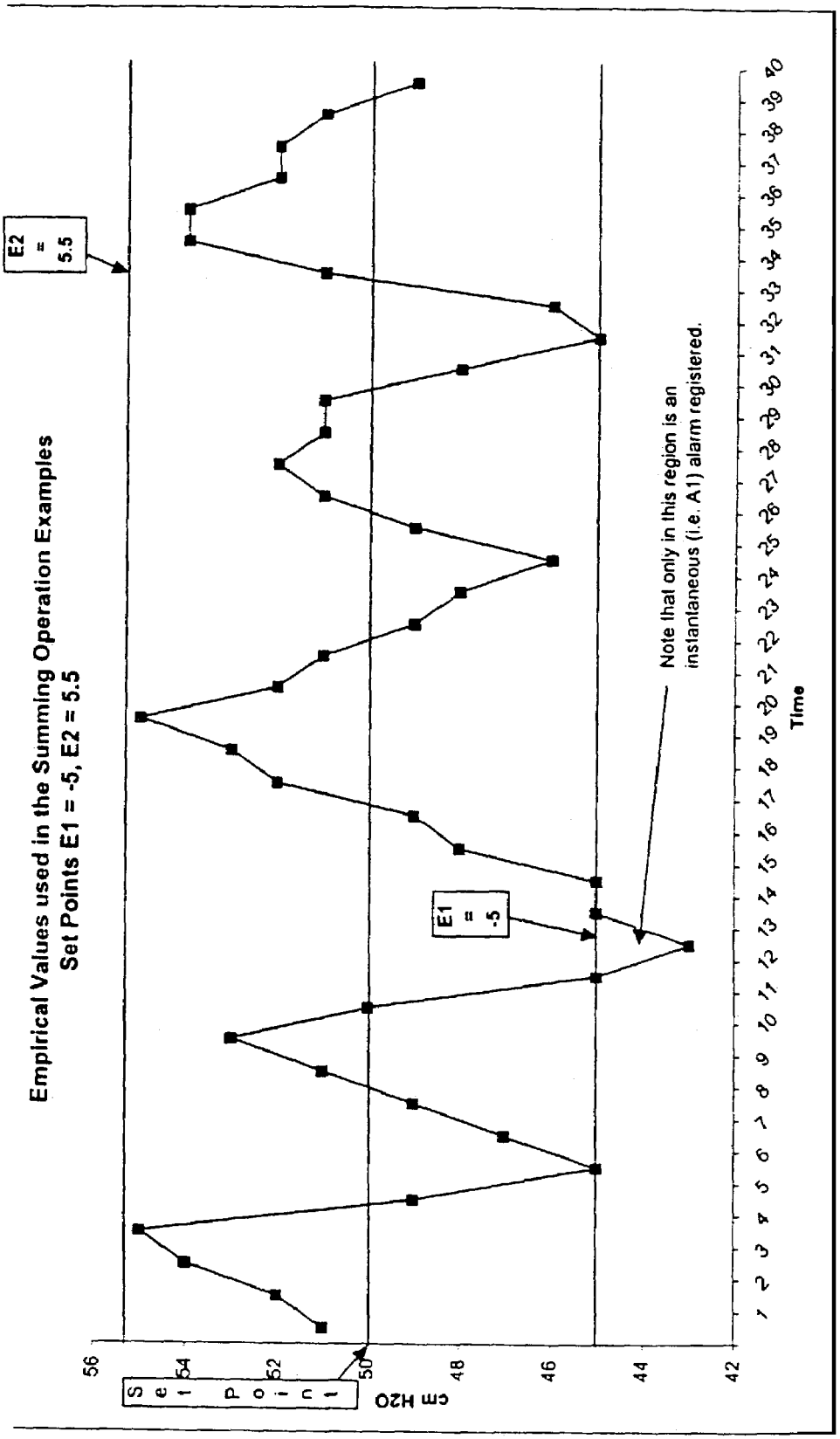

Alarm A2 is a rate-related alarm that is determined (i) by a window-related value ET (explained below) and (ii) a calculated mean (Y) based on successive samples of the detected waveform of varying LMA-inflation pressure, wherein the samples are taken for each successive 0.1-second sampling interval, and are effectively integrated and stored as absolute values in a word-summing array circuit, as shown in FIG. 3; each of the absolute values is taken for its sampled magnitude with reference to a steady base line, conveniently the set-point value, as shown in FIGS. 6A and 6B. If the mean value, i.e., the sum of the most recent successive thirty-two integrated samples, divided by 32 (61, FIG. 3A), exceeds the value ET, as further explained below, the A2 alarm will issue, such as "CHECK ANAESTHESIA", to the anaesthetist by a combination of visual and/or audio signals. The anaesthetist is thereby further alerted to make an immediate corrective response, as by increasing the strength of the anaesthetic which is being administered to the patient. ET is calculated by adding the absolute values of E1 and E2, and dividing the sum thereof by a selected constant k, i.e., $$ET = \frac{1}{k}[|E1| + |E2|],$$

wherein k is a selected value in the range 3 to 6 (and preferably 4), it being explained that with k=4, the "divide-by-4" relationship establishes a preferred practical safety factor by means of which the "CHECK ANAESTHESIA" alarm is reliably issued even though the instantaneous-type alarm A1 may not have issued.

As shown in FIG. 3, at the conclusion of each 3.2-second sampling period, the oldest sample is discharged and the latest sample is incorporated in the new calculation of mean value for the next 32-sample comparison to ET.

Thus, for example, the anomaly depicted in FIG. 5A, which is illustrative of a pain-stimulus event observed in a surgical procedure, will be seen to give rise to determinations which are major departures from the normal situation depicted in FIG. 5. If an initial sample traverses one of the boundaries of the alarm window, the first alarm A1 will be triggered, and the second alarm A2 may not immediately be triggered. However, the integration and mean-value development described above can result in a "CHECK-ANAESTHESIA" alarm A2, even if a threshold-traverse needed for the first alarm A1 may not have occurred. In addition to these two alarms, the anaesthesiologist may monitor continued progression in the form of percent awakening that can be displayed as shown in FIG. 1B, the same being discussed below under the heading, "Display Features".

Although the graph of FIG. 5A reflects interplay of various reactions, it is particularly noted that, once such reactions are detected, major transient departures from the set-point SP are eliminated within substantially 30 seconds by prompt administration of additional anaesthesia.

D.2. Display Features

The display 49 contains a window of time through which the continuously varying signal, such as that shown in FIGS. 5, 5A, 6B, 6D, and 7, will show the latest single full minute of regulated pressure variations, passing into the window at its left-hand margin, and passing out of window viewability at the right-hand margin.

Figure 1A:
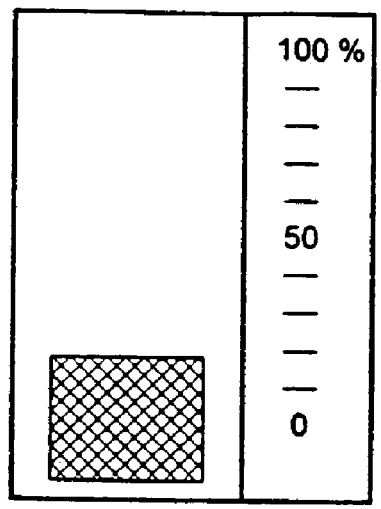
FIG. 1A displays a first of two typical readouts of a percent-awakening feature, which may comprise a portion or all of a display screen.
Figure 1B:
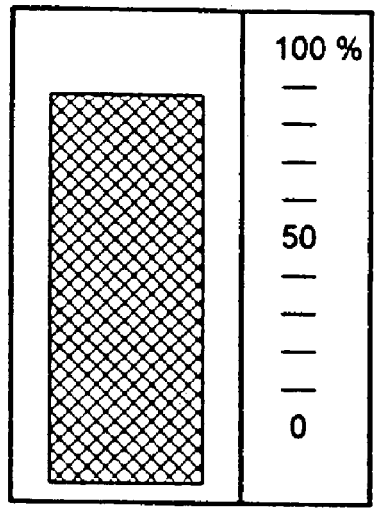
FIG. 1B is a similar display for a second and subsequent readout of the percent-awakening feature.

An additional method for displaying the results of the above-described integration/summation process (mean value) is shown in FIG. 1A and FIG. 1B, where these two displays in the course of time indicate a progression, from a deeper level of anaesthesia, shown in the first example FIG. 1A, to an incipient level approaching awakening, shown in the second example FIG. 1B. The display preferably consists of a bar chart that shows, as on a percent scale, the output of the successively integrated function described above. The initial value of this continually-updated display is established for each individual patient, preferably after the anaesthetized patient is positioned by the surgeon on the operating table, in readiness for surgery. The parameter equivalent to a 100% display reading will equate to the full value of ET, at which point the "CHECK ANAESTHESIA" alarm will issue.

Also provided for utilization by anaesthetist and/or other personnel studying a particular surgical procedure is the ability to connect separate microprocessor or other data-presentation means to a computer interface 41, thus providing for the monitoring, recording and analysis of system indicators on separate electronic media, as when more sophisticated recording and analyses are desired.

D.3. Autoscaling of Alarm Window

It has been discovered that the monitoring function of the system of the invention can be made more efficient by allowing the size of the check-anaesthesia alarm window to be automatically reduced (or autoscaled), thereby providing an advantage of faster alarm threshold (i.e., E1 and E2) adjustment and therefore more accurate monitoring of anaesthesia level. To accomplish such autoscaling of the check-anaesthesia alarm window, both the upper and the lower peak amplitudes from at least eight consecutive waveforms are sampled, averaged, and mean values for the upper and lower peaks are determined. Two checks for validation of peak values are used; all eight upper and lower limits that are sampled must be obtained during the same two-minute sampling period, and small oscillations that may otherwise be identified as peaks can be eliminated by operator input of a preset minimum amplitude.

These upper and lower peak amplitudes define, in essence, an "envelope" that typically decreases in accordance with the patient's compliance to positive pressure ventilation (IPPV), as the patient becomes more anaesthetized. In considering the usefulness of a need to reestablish alarm thresholds in the sense of following an envelope of decreasing amplitude (or size), it must be remembered that the patient's respiratory pressure is commonly reduced as the patient becomes more compliant. Limiting the alarm thresholds (i.e., E1 and E2) has been found to be an effective and desirable method for automatically reestablishing the sensitivity of the monitoring device so that pain-stimulus derivation will continue to be detected, despite a reduction in envelope size.

As a safety consideration, the preferred device will allow the autoscaling feature only to reduce, and not to automatically enlarge, the check anaesthesia alarm window.

The amount by which autoscaling can vary E1 and E2 is fully adjustable between zero and one hundred percent, with a default value of fifty percent. It is interesting to note that such autoscaling frequently causes E1 and E2 to no longer be symmetrical about set-point SP, similar to the alarm window shown in FIG. 6B.

D.4. Re-Centering Operation System

As described above, the system of the invention will automatically compensate for leaks and gains in monitored inflation air. Because the stepper motor controller and driver 47 maintain a count of direction commands issued to the stepper motor 33, the stepper motor driver 47 is able to and will so indicate when piston 27 has reached an end of its travel. Such-indication will operate switches 42 to position "1" and trigger the initiation of a "reset" function governed by the controller 60, for start-up, centering, and reset. Depending on the reset command sent by motor controller 47, i.e., when an anomalous condition requires a replenishment or purge of piston air, appropriate action will be taken by the controller 60. For example, when the reset function requires that air be added to the system, the controller 60 will (i) deactivate solenoid valve V1, returning it to its normally closed state; (ii) activate solenoid valve V2 to an open condition; and (iii) send appropriate signals to stepper motor controller and driver 47, thereby causing piston 27 to be driven by motor 33 at high speed to exhaust excess "air" (or, where appropriate, taking in additional fresh air) via port 44. The memory of the controller 60 will have retained from the system start-up procedure described above, the number of pulses required to drive piston 27 to its or midposition (L/2).

In normal monitoring and regulatory operation of the described system, there will be little call for great displacements of piston 27. But large displacements can occur, for example, a loss of monitored inflation air may be caused by surgical-knife contact with the inflated LMA ring 19. This condition will be observed by the system, calling for continued supply of either additional or reduced inflation air depending upon whether lug 37 coacts either with limit switch LS1 or LS2, thereby indicating that piston 27 has reached the end of its travel. Such limit-switch signal will cause: (i) switches 42 to bypass the FIG. 3 control circuit; (ii) the sending of an alerting notice to the anaesthetist, as in the form of an audible alarm, with visual display of the message, "CHECK FOR LEAKS"; and (iii) the triggering of the reset function of controller 60, as is described above.

The above description highlights an additional advantage of the automated device in that it will, as described, replenish the volume of air in cylinder 26 within approximately 7.2 seconds, which is significantly faster than typically possible by manual operation. Despite such favorable automatic recovery time, the pressure adjustments made by the system are sufficiently discrete to allow pressure regulation of the smallest LMA cuff without causing undue pressure rebound within the small volume.

All such operations are automatic, as are the warnings or alarms that are part and parcel of assuring maintenance of set-point pressure, for as long as the circumstances may require for a given patient, or for a given LMA size that the patient is deemed to require.

CONCLUSION

The described device and its method of use will be seen to have achieved all stated objects, acting as a controller of LMA-cuff pressure, as a device that will monitor and correct for leaks, as a monitor of a possible pain stimulus to the patient's neuromuscular system while the patient is anaesthetized for the course of a surgical procedure, and as a monitor to prevent a patient from remaining under the effect of a muscle-relaxant while not being adequately anaesthetized. In particular:

1. The device is controlled by a microprocessor unit which performs all tasks including, but not limited to, diagnostic checks, motor and valve operation and control, and pressure measurement.

2. The device includes a graphic display and control unit as well as an interface for advance monitoring and control thus permitting data evaluation with different commercial software packages.

3. The device provides instantaneous values of LMA-cuff pressure via redundant pressure sensors that are pneumatically connected to the inflation line of the LMA cuff. For safety reasons, the pressure measurement is taken by redundant transducers, of which an automatic comparison is continuously performed.

4. The device normally operates with the same volume of air, seeking maintenance of set-point pressure for LMA-cuff inflation, wherein for each sampling measurement of LMA-cuff pressure, departure from set-point value causes piston displacement in the direction to reduce to zero (or to substantially zero) the departure of measured pressure from set-point pressure.

5. The device is so detachably connected to the inflation/deflation air line of the LMA as to permit normal LMA-patient installation procedures, without relying upon any of the automatic features of the device. As a consequence, the patient may be "prepped" for the operation by having the LMA installed, with inflated cuff, and completely checked to assure that it has been properly installed, before the patient enters the operating room, thus relying on a check valve to hold inflation pressure, prior to device-connection of the patient and the inflated-LMA cuff.

6. If, for any reason, the system is not working or is not working properly, the system will revert to a fail safe mode, with operational valves returning to their normally closed condition, thereby maintaining LMA inflated-cuff pressure.

7. In its normal regulation mode, system-pressure sampling is at every one-tenth (1/10) of a second, with ample time to accomplish evaluation against set-point pressure, and issuance of a train of pulses is for such piston displacement as will achieve a measured-pressure correction to substantially set-point pressure. Normal regulation occurs if evaluation of a pressure sample exceeds a threshold value of ±0.5-cm H2O from an adjustable set-point value.

8. It is important to emphasize that normal operation of the described LMA system exhibits major advantages which flow from the fact that the system works with a virtually closed volume of air. An increase of measured pressure will rapidly cause displacement of a portion of the volume of air from the LMA cuff and into the volume defined between the piston and the head end of the cylinder; and this volume of air will be returned to the LMA cuff virtually as soon as measured pressure is detected to have decreased. This sharing of the same volume of air is always true, except when, due to a leak or to some other unexpected event, the piston reaches the end of its travel, as such is tracked by position-counter operation maintained within the stepper motor controller or upon reaching of one of the limit switches, at which point the piston will be repositioned, with an air discharge or an uptake of fresh air, as the occasion may dictate, all while the LMA cuff can retain its inflation pressure.

9. Once stabilized, the described system is found to be sensitive to very small pressure variations (in the order of 1/16-cm H2O) and can be quick and precise in its response without contaminating the monitoring function with time constant or hysteresis transients. It is believed that such response is achieved because of the described stepping motor and lead-screw drive, in combination with normal regulating displacements within the virtually closed volume of air. Reliance on the virtually closed volume of air translates into involvement of only one time constant in the increasing or in the decreasing of intra-cuff pressure in the LMA.

10. As an aid to the anaesthesiologist and in the course of a surgical procedure on a patient, the described system permits several concurrently operative algorithms to process, in real time or in close to real time, the anaesthetized patient's initial, incipient and totally involuntary muscular symptoms of arousal from induced sleep and/or paralyzed state, via sensitive response to muscular action observed around the patient's laryngeal inlet and/or at contact with the patient's hypopharynx. Provision is made for audibly and visually alerting the anaesthesiologist to detected approach of patient awakening, in good time to "check anaesthesia" and to institute corrective measures without patient awakening. The described system is seen to be inherently capable of adapting itself to enhanced precision of detecting loss of depth of anaesthesia as it progressively narrows the focus of its attention to a predetermined margin of safety in evaluating observed fluctuations in LMA-inflation pressure.

11. The monitoring function of the described system may be useful in detecting and providing means to guard against a circumstance in which the patient, who has been administered both an anaesthetic and a separate muscle relaxant (e.g., atracurim or vecuronium), has the anaesthetic wear off while remaining immobilized due to the continuing effect of only the muscle relaxant. Such circumstance has been known to be highly unpleasant due to the patient's inability to reveal that the patient is experiencing the full effect of surgical manipulations. The LMA monitoring system may be useful as a guard against such an event, in view of the more limited effect of some muscle relaxants upon pharyngeal constrictor muscles, which the LMA cuff 19 necessarily contacts with its ability to monitor for muscle activity. Others have observed that the contraction curve of the pharyngeal constrictor muscles is unchanged during partial paralysis caused by a common muscle relaxant. See, Ericsson, et al., *Functional Assessment of the Pharynx at Rest and during Swallowing in Partially paralyzed Humans*; Anaesthesiology, V 87, No. 5, November 1997.

12. It is noted further that although the monitoring and other detecting functions of the described system are preferably in the context of LMA inflation response, the LMA context is merely illustrative of use of a suitable inflated device within the pharyngeal cavity to respond to and produce appropriate warning of the muscle action in the region of inflated-material contact with one or more regions of muscle action.

13. And it is also noted further that preferred numerical values stated herein as 4, 8, 32, etc. are only illustrative and that they have been selected as power values of 2, in view of the preferred reliance on digital-system operation.

What is claimed is:

1. A combination of a laryngeal mask airway device and an apparatus for automatically monitoring the anaesthetized status of a patient in the course of a surgical procedure on the patient when the laryngeal mask airway device is installed in the patient, the laryngeal mask airway device comprising an airway tube having a distal end and an inflatable mask disposed at the distal end for sealing engagement around the laryngeal inlet, with communication to the patient's lungs via the tube and through the mask, said mask having a flexible tubular inflation line accessible externally of the patient; said apparatus comprising:
   (a) a pressure transducer detachably connected to said inflation line for producing an electrical-signal output pursuant to instantaneous pressure in the inflatable mask indicative of a tone of muscles in the patient's larynx or pharynx as a function of time during the surgical procedure;
   (b) pressure evaluating means including means for computing a value according to a function of changes in the pressure over time; and
   (c) said pressure-evaluating means producing an alarm-signal output if the value departs from a predetermined range.

2. Apparatus according to claim 1, further including display means for continuously displaying transducer-observed pressure as a function of time, wherein the predetermined range may be adjusted based at least in part on visual monitoring of said display means during a period after administration of anesthetic to the patient and before commencement of surgery.

3. A method of using a laryngeal mask airway device to monitor the anaesthetized status of a patient in the course of a surgical procedure on the patient, wherein the device comprises an airway tube having a distal end with an inflatable mask at the distal end for sealing engagement around the laryngeal inlet and for establishing exclusive communication to the patient's lungs via the tube and through the mask, said mask having a flexible tubular inflation line accessible externally of the patient; said method comprising the steps of:
   (a) Selecting and installing the device in the patient with mask inflation to establish a sealed engagement around the patient's laryngeal inlet;
   (b) Selecting and connecting a pressure-sensitive device to said inflation line, whereby to continuously monitor instantaneous inflation pressure fluctuations indicative of a tone of muscles in the patient's larynx or pharynx as a function of time during the surgical procedure;
   (c) Analyzing fluctuations in sensed pressure for a period of time prior to commencement of the surgical procedure to establish an acceptable range for the sensed pressure fluctuations;
   (d) Commencing the surgical procedure; and
   (e) Issuing a warning if a measure of the magnitude of the sensed pressure fluctuations over time exceed the acceptable range.

4. A method of using a laryngeal mask airway device to monitor the anaesthetized status of a patient in the course of a surgical procedure on the patient, wherein the device comprises an airway tube having a distal end with an inflatable mask at the distal end for sealing engagement around the laryngeal inlet and for establishing exclusive communication to the patient's lungs via the tube and through the mask, said mask having (i) a distal end configured for locating contact with the patient's hypopharynx and (ii) a flexible tubular inflation line accessible externally of the patient; said method comprising the steps of:
   (a) Selecting and installing the device in the patient with mask inflation to establish (iii) a sealed engagement around the patient's laryngeal inlet and (iv) distally locating mask engagement with the patient's hypopharynx;

(b) Selecting and connecting a pressure-sensitive device to said inflation line, whereby to continuously monitor instantaneous inflation pressure fluctuations indicative of a tone of muscles in the patient's larynx or pharynx as a function of time during the surgical procedure;

(c) Analyzing fluctuations in sensed pressure for a period of time prior to commencement of the surgical procedure to establish an acceptable range for the pressure fluctuations;

(d) Commencing the surgical procedure; and (e) Issuing a warning if a measure of the magnitude of the sensed pressure fluctuations over time exceed the acceptable range.

5. A method of using a laryngeal mask airway device to monitor the anaesthetized status of a patient in the course of a surgical procedure on the patient, wherein the device comprises an airway tube having a distal end with an inflatable mask at the distal end for sealing engagement around the laryngeal inlet and for establishing exclusive communication to the patient's lungs via the tube and through the mask, said mask having a flexible tubular inflation line accessible externally of the patient;

(a) Selecting and installing the device in the patient with mask inflation to establish a sealed engagement around the patient's laryngeal inlet;

(b) Selecting and connecting a pressure-sensitive device to said inflation line, whereby to continuously monitor instantaneous inflation pressure indicative of a tone of muscles in the patient's larynx or pharynx as a function of time during the surgical procedure;

(c) Commencing the surgical procedure;

(d) Analyzing fluctuations in pressure for a period of time after commencement of the surgical procedure to establish an acceptable range for the pressure fluctuations; and (e) Issuing a warning if a measure of the magnitude of the sensed pressure fluctuations over time exceed the acceptable range.

6. The apparatus of claim 1, wherein the value is based on a mean of measured pressure deviations from a set point pressure over a selected time interval.

7. The method of claim 3, claim 4, or claim 5, wherein the measure of the magnitude of the sensed pressure fluctuations over time comprises a mean of the sensed pressure deviations from a set point pressure over a selected time period.

8. The method of claim 3, claim 4, or claim 5, further including monitoring a visual display of the sensed pressure over time, and adjusting the acceptable range based at least in part on the monitoring.

* * * * *